United States Patent
Yamazaki et al.

[11] Patent Number: 5,497,776
[45] Date of Patent: Mar. 12, 1996

[54] ULTRASONIC IMAGE DIAGNOSING APPARATUS FOR DISPLAYING THREE-DIMENSIONAL IMAGE

[75] Inventors: Tatsuo Yamazaki, Sagamihara; Tomonao Kawashima, Hachioji, both of Japan

[73] Assignee: Olympus Optical Co., Ltd., Tokyo, Japan

[21] Appl. No.: 285,734

[22] Filed: Aug. 4, 1994

[30] Foreign Application Priority Data

| Aug. 5, 1993 | [JP] | Japan | 5-194873 |
| Dec. 3, 1993 | [JP] | Japan | 5-304129 |
| Jun. 13, 1994 | [JP] | Japan | 6-130474 |

[51] Int. Cl.⁶ .................................................. A61B 8/12
[52] U.S. Cl. .................... 128/660.09; 128/662.06; 128/916
[58] Field of Search ................... 128/660.04, 660.09, 128/660.1, 662.06

[56] References Cited

U.S. PATENT DOCUMENTS

| 5,107,844 | 4/1992 | Kami et al. | 128/662.06 |
| 5,255,681 | 10/1993 | Ishimura et al. | 128/662.06 |
| 5,257,628 | 11/1993 | Ishiguro et al. | 128/662.06 |

FOREIGN PATENT DOCUMENTS

| 2265536A | 10/1990 | Japan . |
| 4279156A | 10/1992 | Japan . |
| 515538A | 1/1993 | Japan . |

Primary Examiner—Francis Jaworski
Attorney, Agent, or Firm—Stevens, Davis, Miller & Mosher

[57] ABSTRACT

An apparatus for displaying an ultrasonic three-dimensional image of a living body including an ultrasonic vibrating element arranged at a distal end of an ultrasonic probe rotatably and linearly movable, a motor for rotating the ultrasonic vibrating element to perform a radial scan on a first cross section, and a stepping motor for linearly moving the ultrasonic vibrating element along a longitudinal axis of the probe to perform a linear scan. By performing the radial scan and linear scan, echo data of a three-dimensional region is picked-up. Prior to picking-up the echo data, the ultrasonic vibrating element is rotated to effect only the radial scan at a cross sectional position at a middle point between a linear scan range, so that a B-mode ultrasonic image is displayed on a monitor. Prior to the picking-up of the echo data, a cross sectional position is set, and during the picking-up of the echo data, the echo data is processed in accordance with the previously set cross sectional position. A marker may be displayed in superimposition upon the B-mode ultrasonic image, so that an operator can confirm whether or not a region of interest can be contained in the displayed three-dimensional image easily and promptly.

28 Claims, 18 Drawing Sheets

FIG_1
PRIOR ART

FIG._2

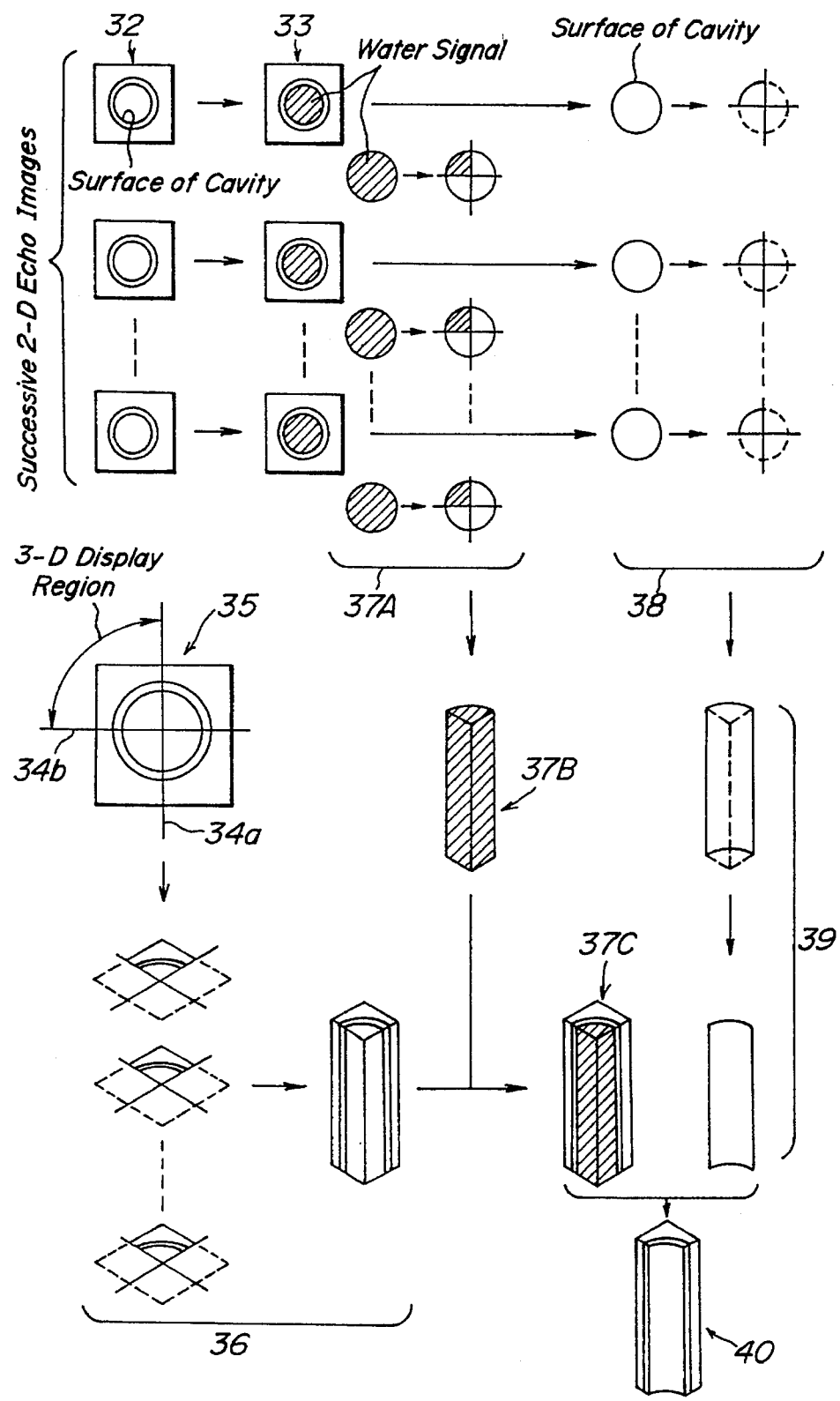
FIG_4

FIG. 5a
FIG. 5b
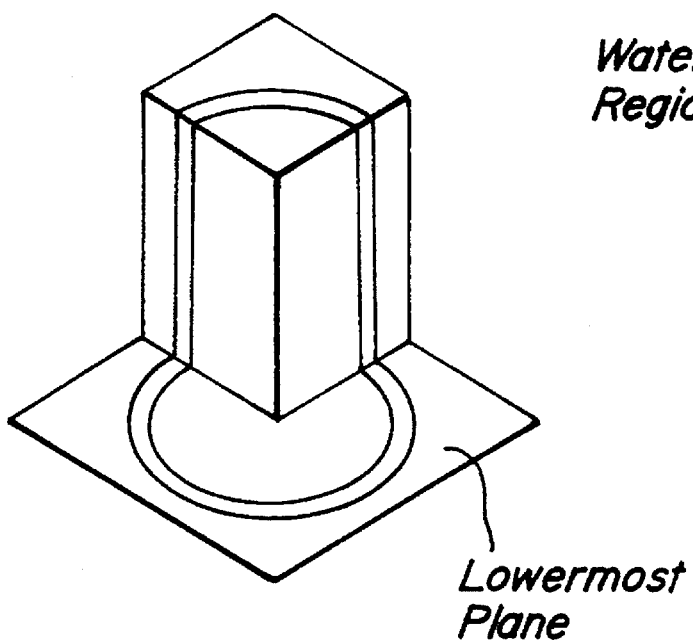
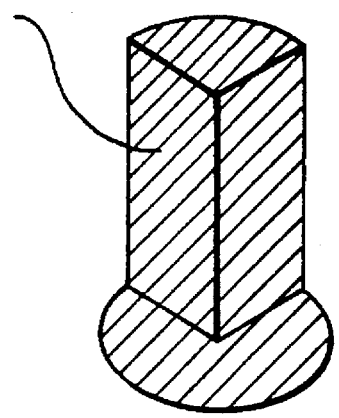
Water Signal Region
Lowermost Plane

FIG_6
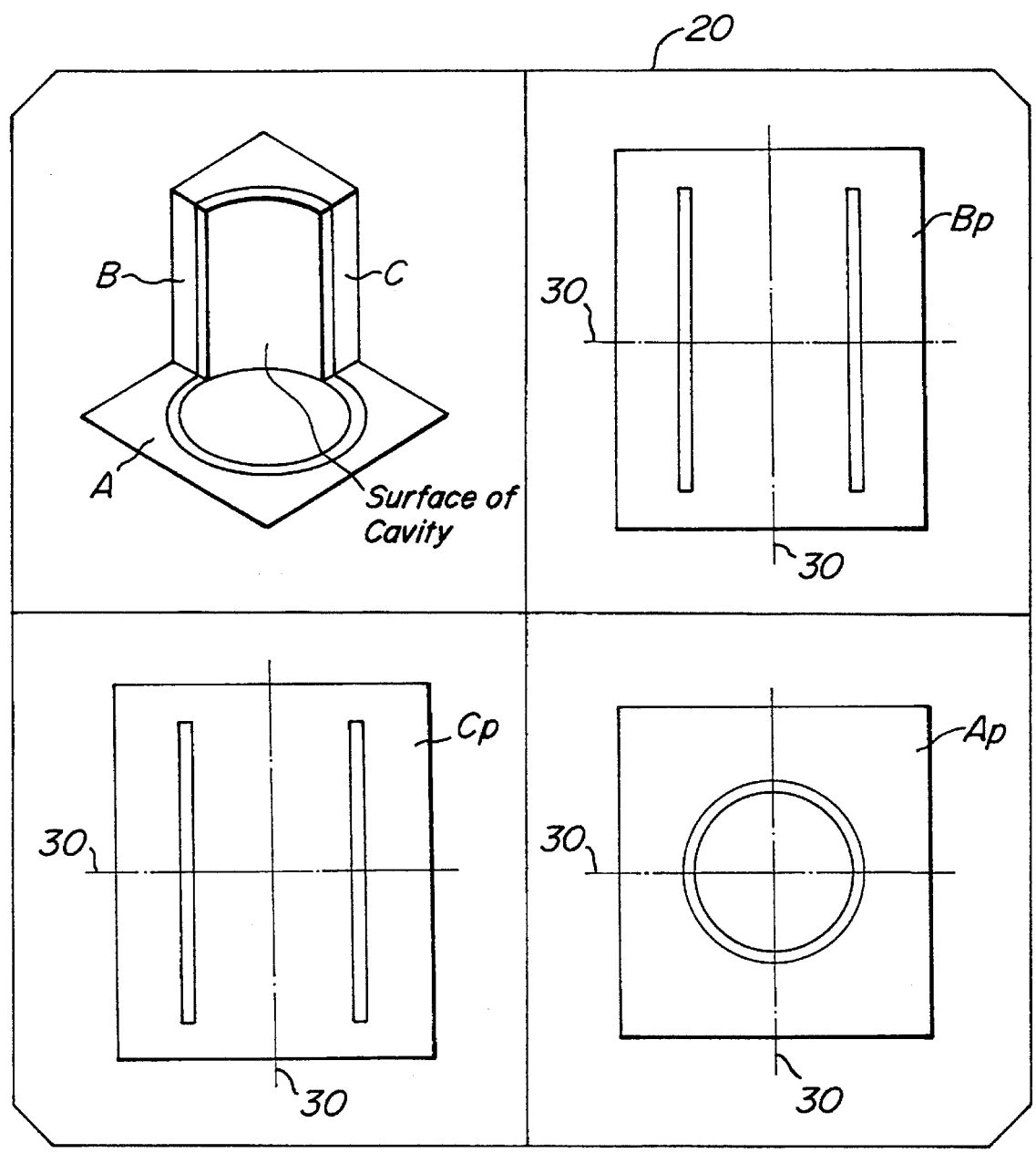

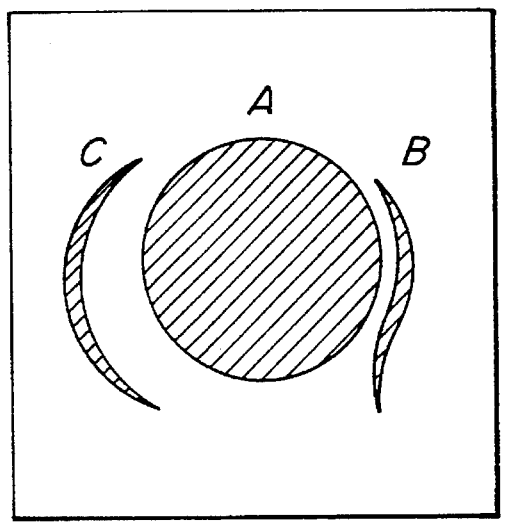
FIG_8a
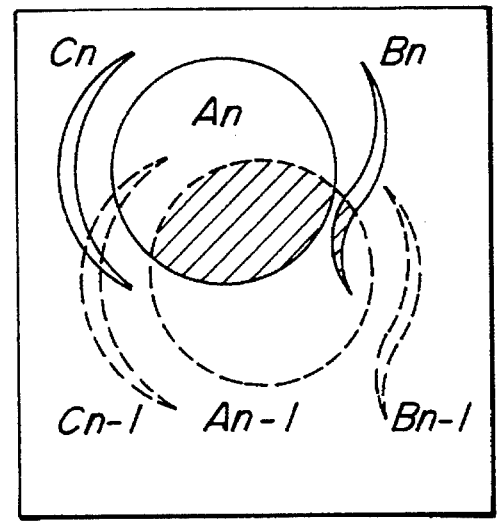
FIG_8b

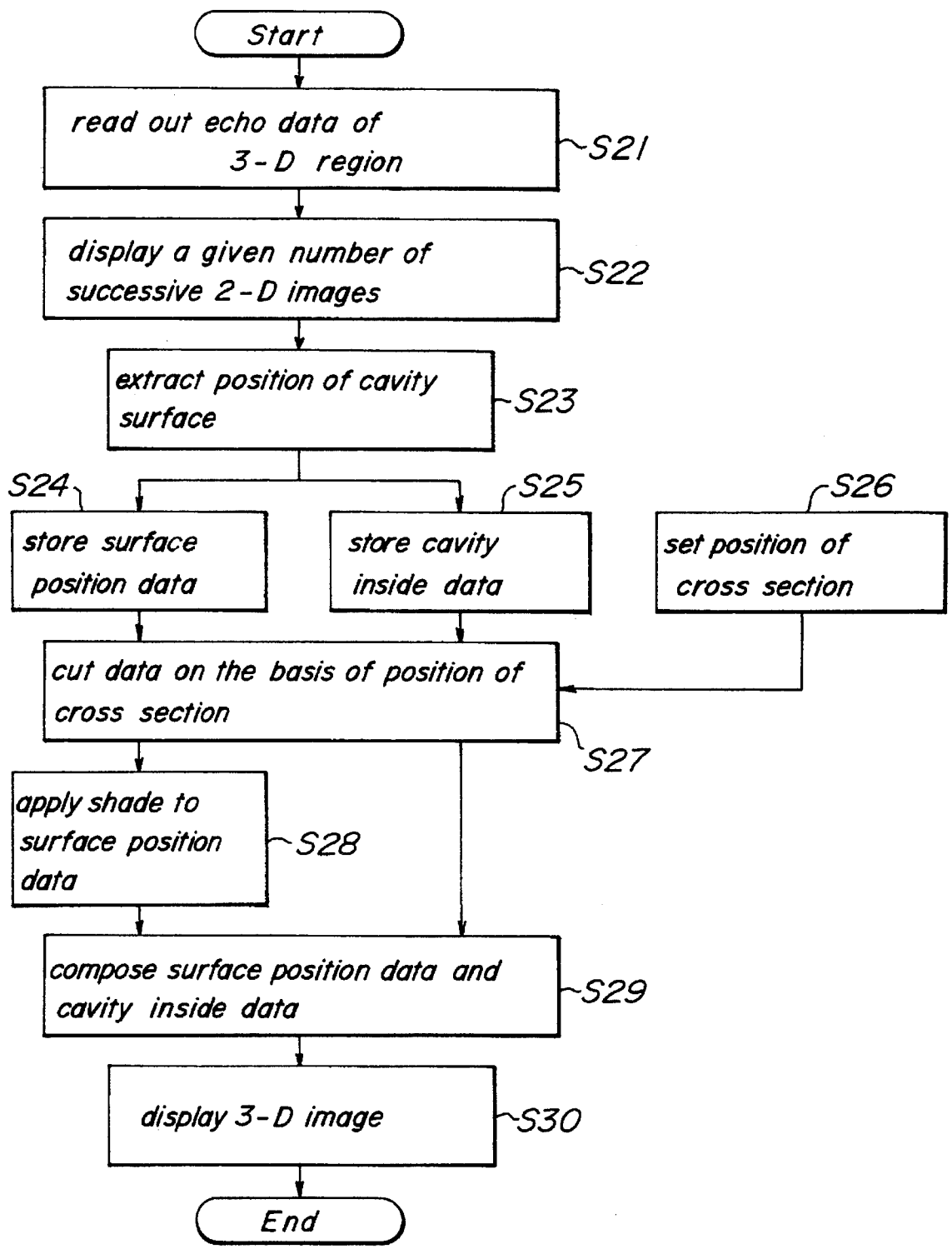

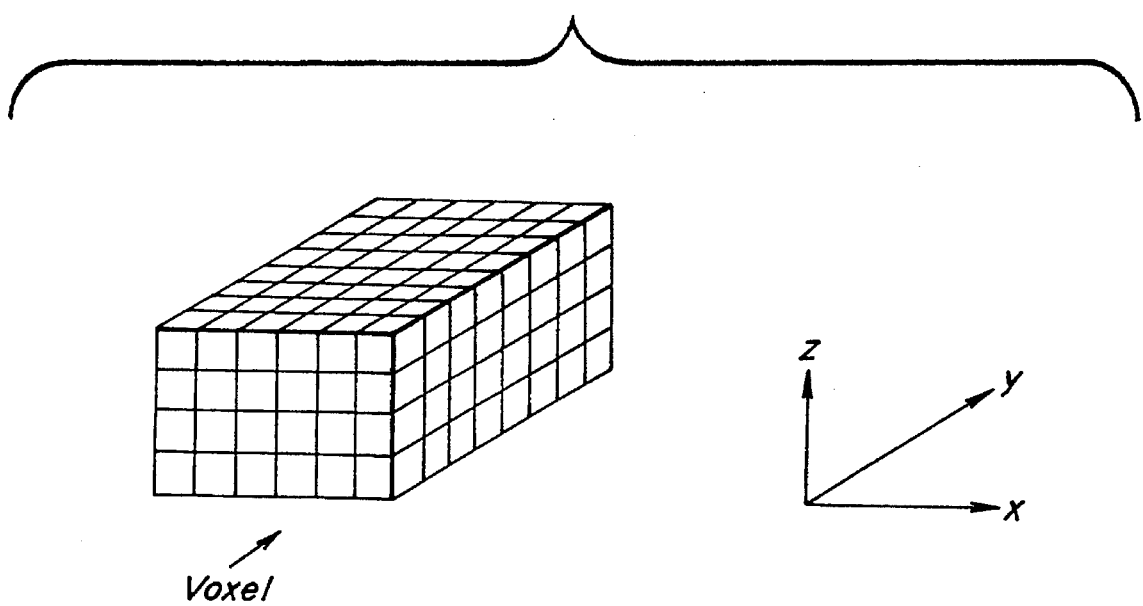
FIG_10
Voxel

FIG_11a
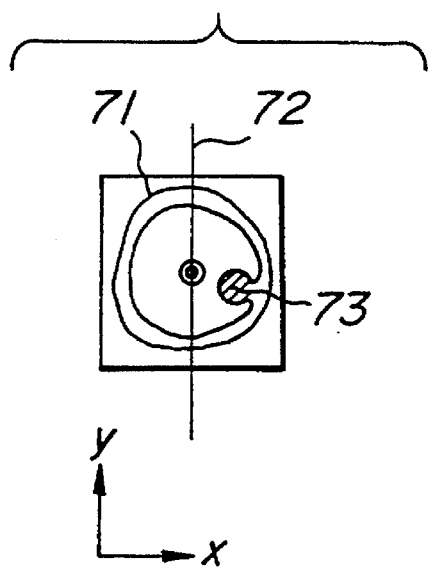
FIG_11b
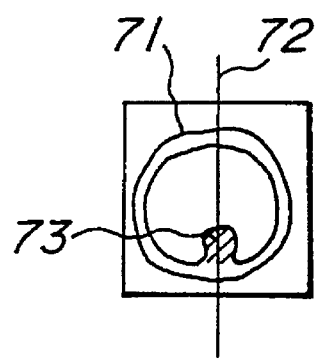
FIG_12
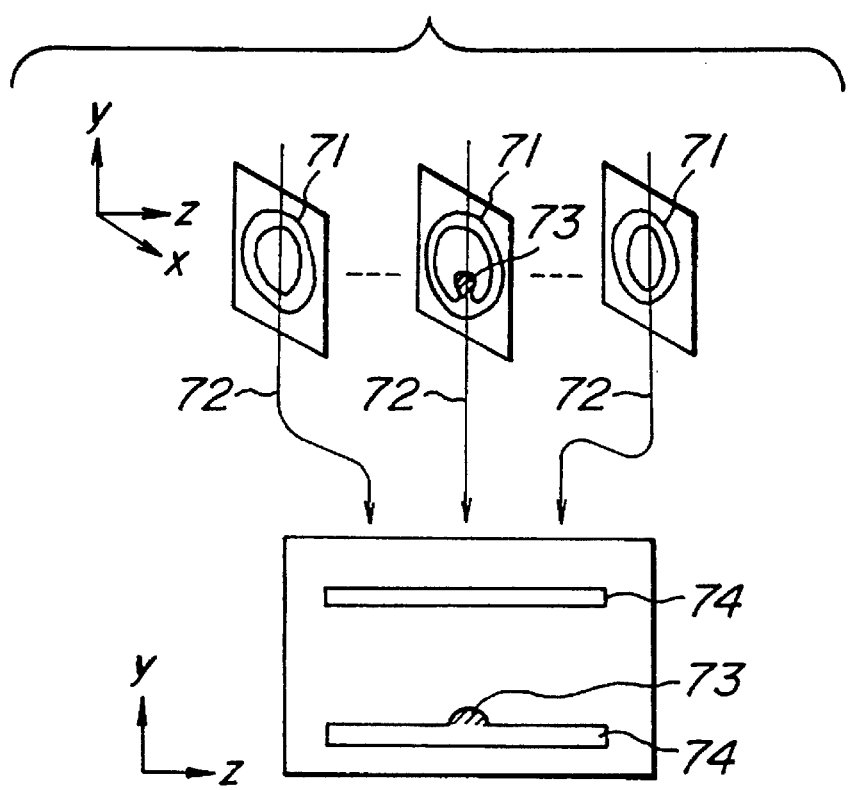

FIG_13a
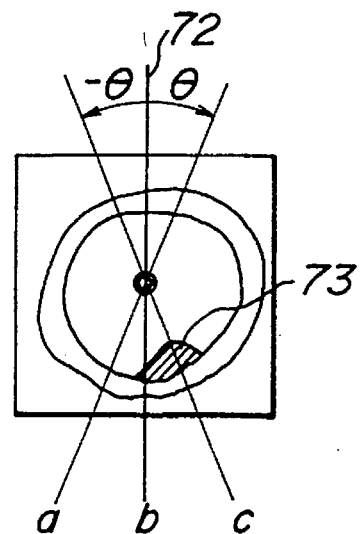
FIG_13b
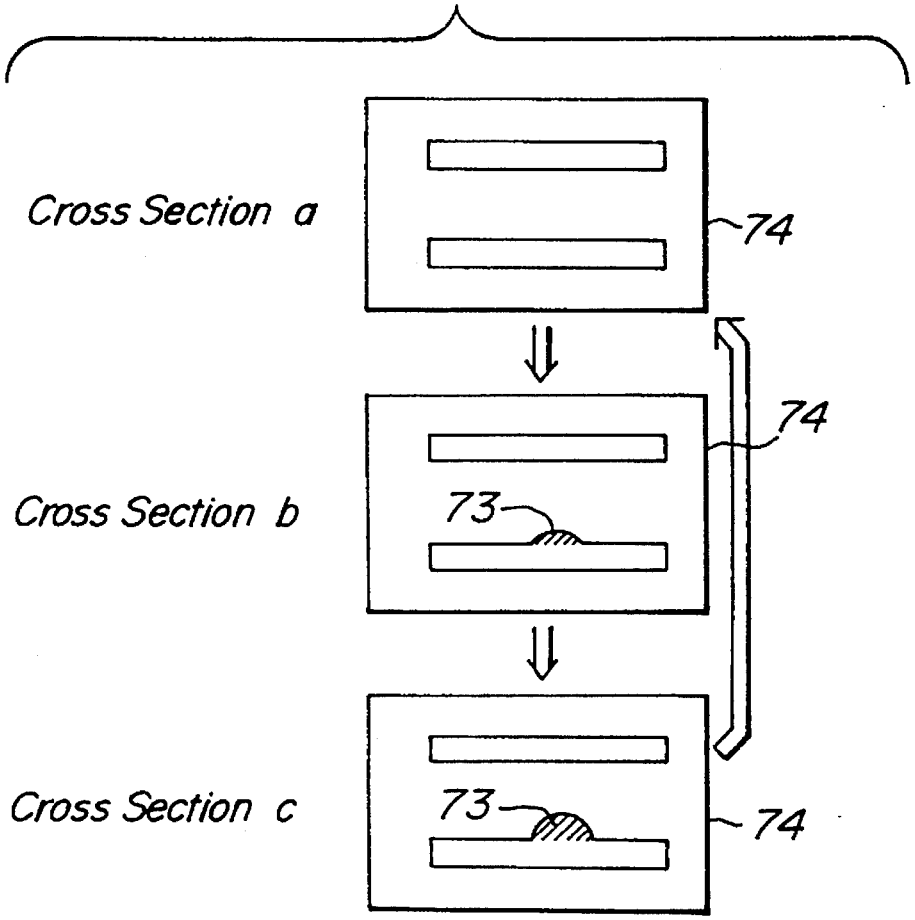
Cross Section a
Cross Section b
Cross Section c

FIG_14
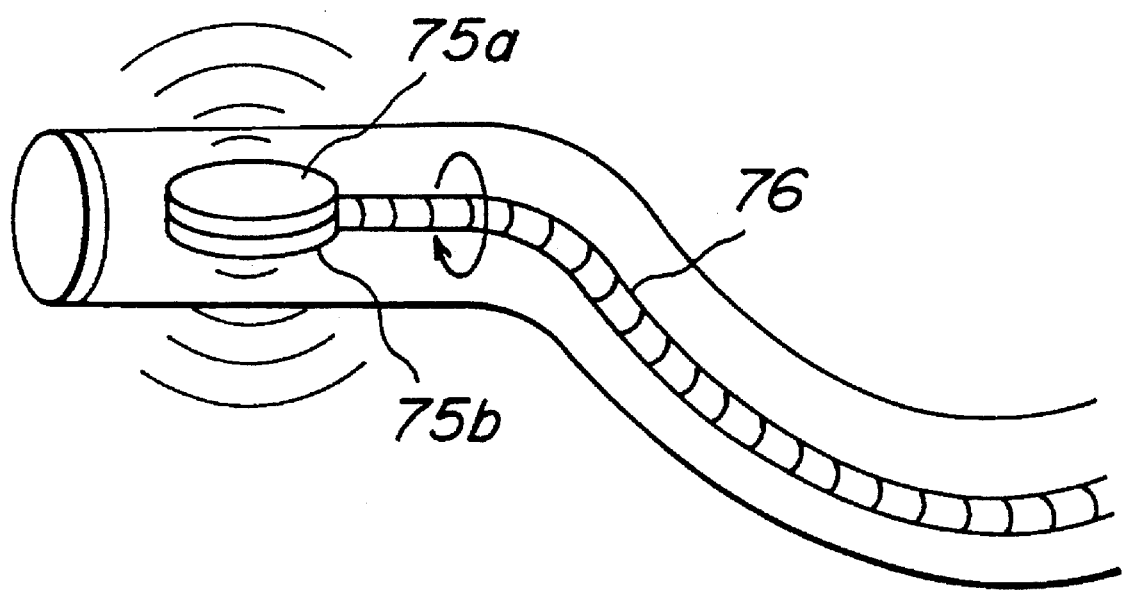

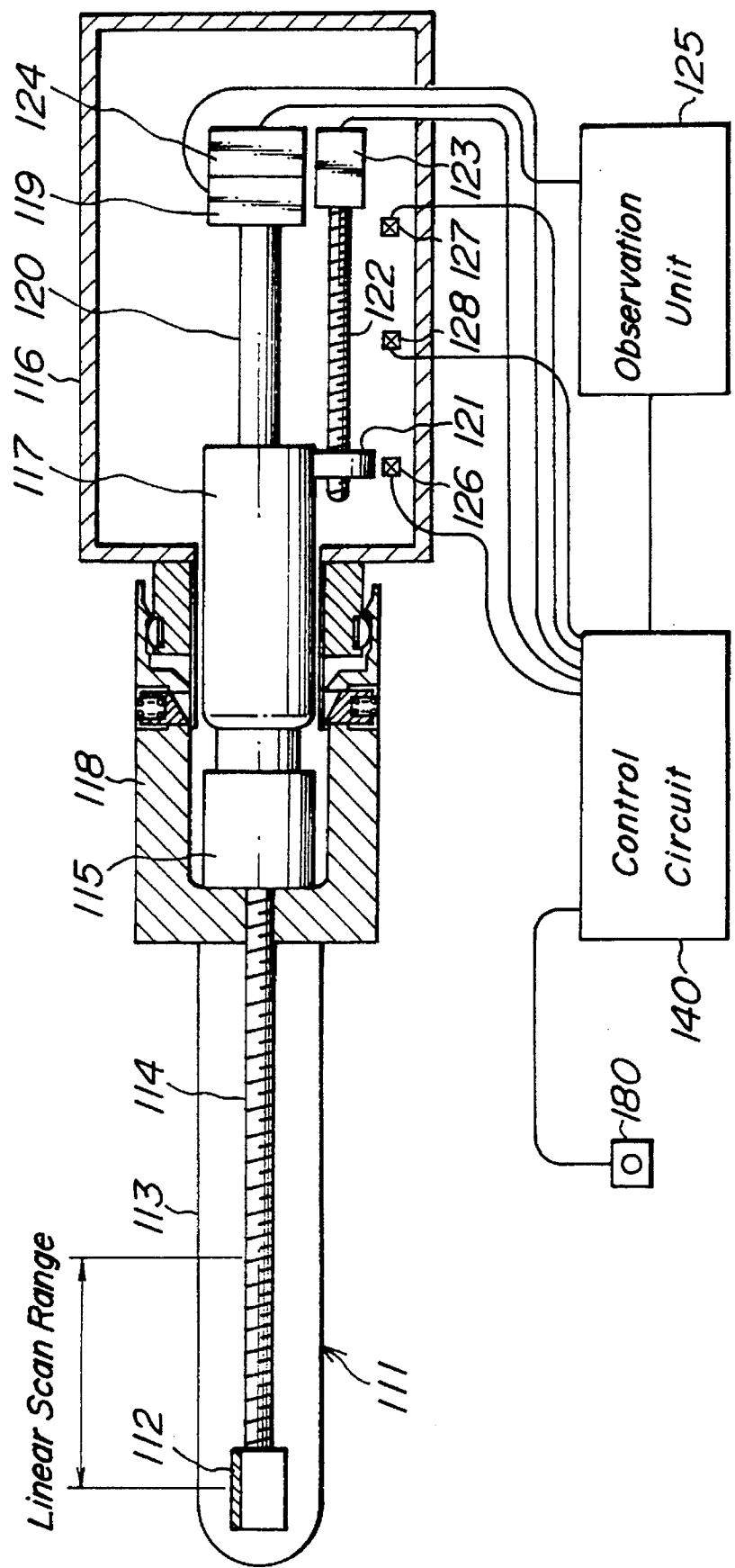

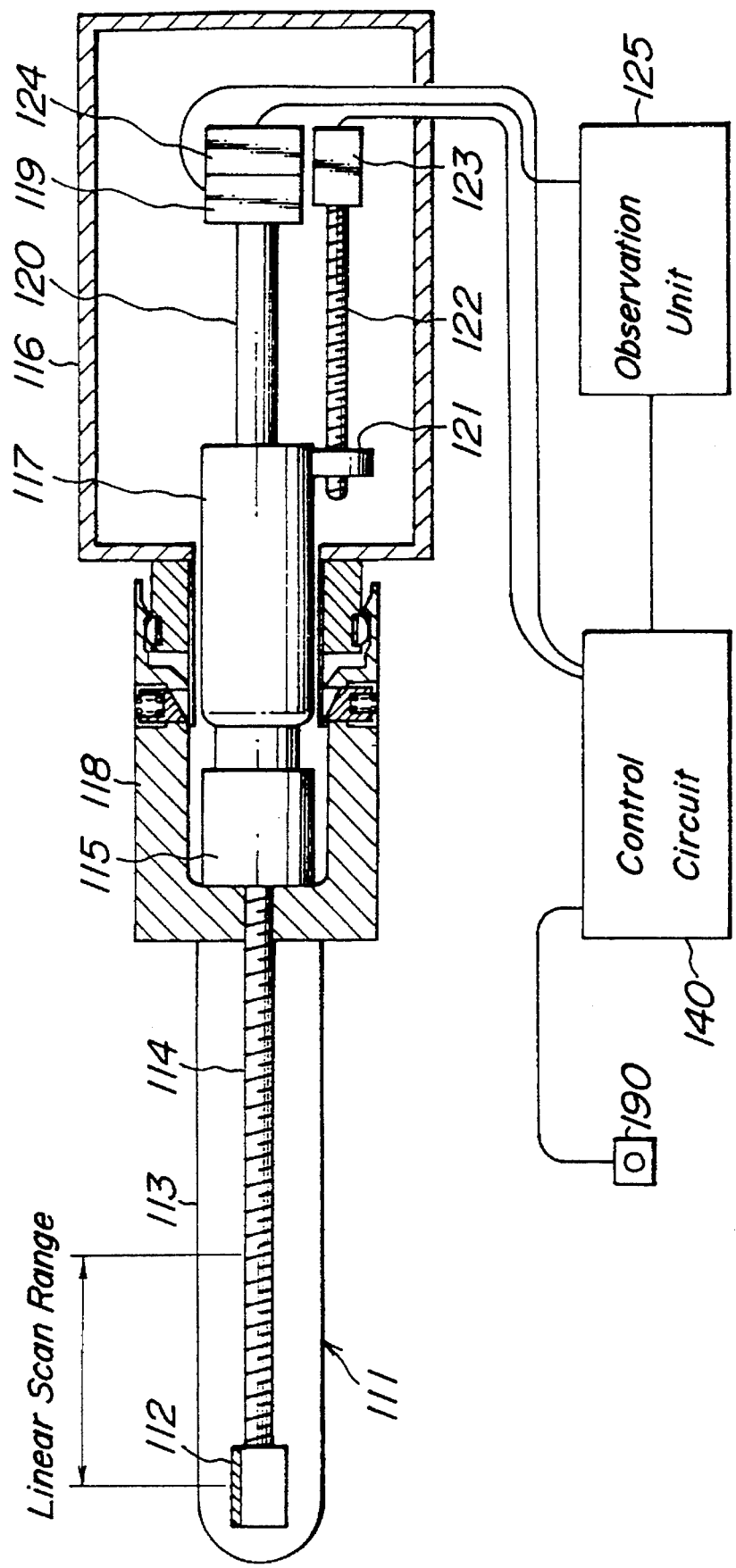
FIG._17

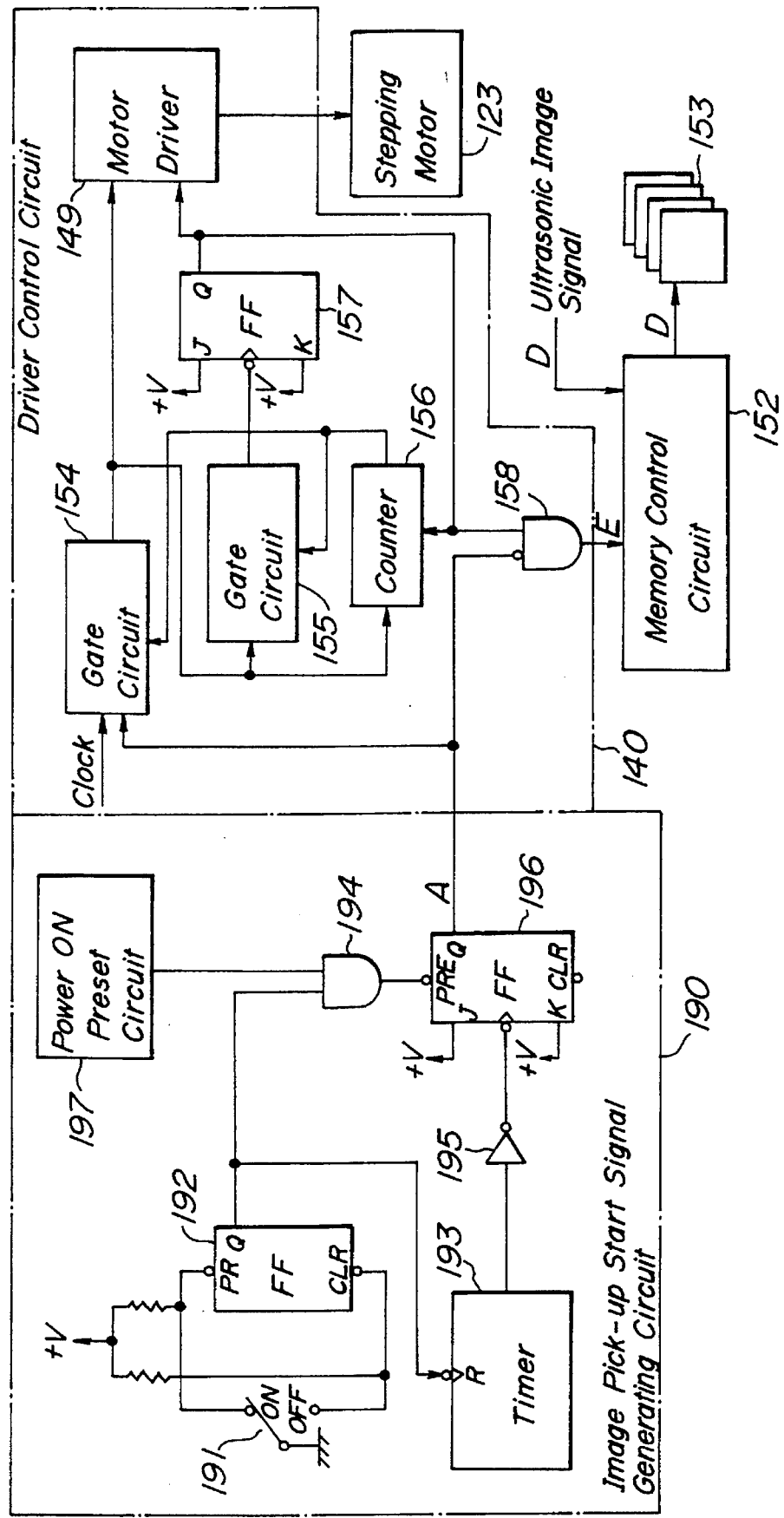
FIG_18

FIG_19
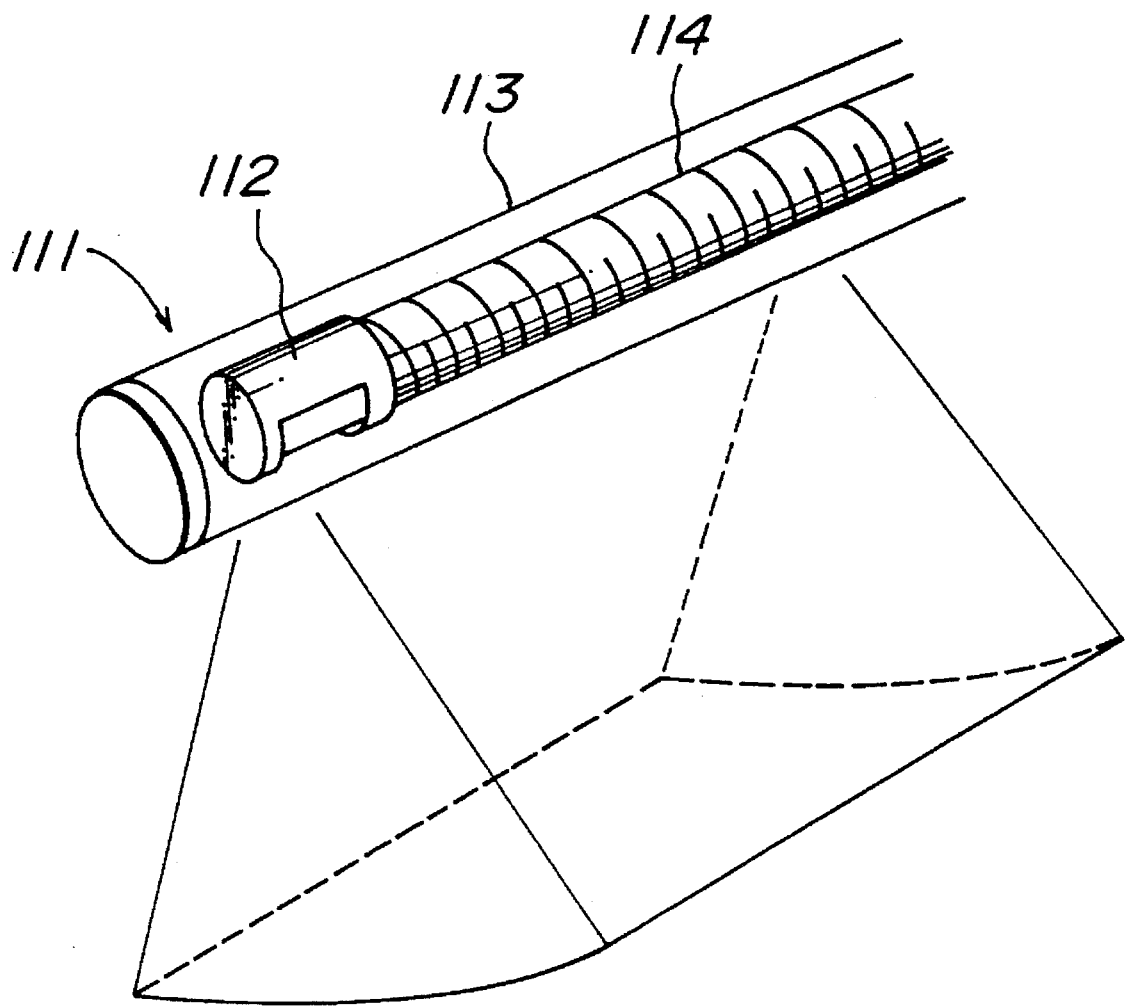

ULTRASONIC IMAGE DIAGNOSING APPARATUS FOR DISPLAYING THREE-DIMENSIONAL IMAGE

BACKGROUND OF THE INVENTION

1. Field of the Invention

The present invention relates to an ultrasonic image diagnosing apparatus comprising an ultrasonic probe for transmitting three-dimensionally an ultrasonic wave toward a living body under inspection and receiving an ultrasonic wave reflected by the living body to generate echo data of a three-dimensional region, an image processing means for processing the echo data to produce a three-dimensional image signal, and a display means for displaying a three-dimensional image of the living body.

In almost all ultrasonic image diagnosing apparatuses of the kind mentioned above, ultrasonic echo data representing a number of mutually parallel cross sectional images is processed to generate the three-dimensional image signal and this three-dimensional image signal is supplied to the two-dimensional display means to display a three-dimensional image. It should be noted that the thus displayed three-dimensional image is not a true three-dimensional image, but is a pseudo three-dimensional image. For the sake of simplicity, in the present specification, the pseudo three-dimensional image is called a three-dimensional image.

In a general three-dimensional image processing apparatus for medical use such as the above mentioned ultrasonic image diagnosing apparatus displaying the three-dimensional image, in order to display three-dimensionally a desired object or cavity within the living body, a so-called shading treatment has been widely utilized. As the shading treatment, there have been proposed various methods such as a volume rendering method in which the shading treatment is performed while maintaining the tone or gray scale based on object information which is inherently contained in the echo data, and a surface model method, in which a surface is extracted by converting the tone of echo data into bivalent data with the aid of a constant threshold level and then the shade is applied to the thus extracted surface.

In case of displaying the three-dimensional image of the object, when use is made of the volume rendering method, it is necessary to treat three-dimensional data having tones, and consequently, an amount of data to be processed becomes very large and a treating time is liable to be long. When the surface model method is used, only the bivalent data of the surface is processed, so that the treating time may be reduced, but the tone based on the object information inherent to the echo data is lost. Thus, an accurate diagnosis might not be performed.

In order to overcome the above mentioned problem, in Japanese Patent Application Laid-open Publication Kokai Hei 4-279156, there is proposed an ultrasonic image diagnosing apparatus, in which a surface of an object is displayed to have a tone and a cross section is displayed as a B-mode image having the tone. In this known apparatus, it is necessary to provide a cross section extracting means for extracting cross sectional image data. The process of extracting the cross sectional image data requires a rather long time period. Moreover, this known apparatus has a drawback that the accuracy of the extraction could be hardly improved.

In the known ultrasonic image diagnosing apparatus, the echo data of a number of mutually parallel cross sectional images is obtained by moving an ultrasonic vibrating element along a longitudinal axis of the probe while the ultrasonic vibrating element is rotated or swung about the longitudinal axis. In the present specification, the mutually parallel cross sectional images are termed lateral cross sectional images, and a longitudinal cross sectional image which is perpendicular to the lateral cross sectional image is derived from the echo data of a number of lateral cross sectional images by the data processing. It is apparent that when the longitudinal cross sectional image is derived after the echo data of all the lateral cross sectional images has been picked-up and stored, the data processing becomes very complicated and requires a relatively long time. In order to avoid such a problem, Japanese Patent Application Kokai Hei 5-15538 has proposed another known apparatus in which both the lateral cross sectional image and longitudinal cross sectional image are displayed simultaneously. However, in this apparatus, a desired area to be inspected might be removed from the longitudinal cross section due to a movement of a living body. As a result, it is uncertain whether a good image for diagnosis can be obtained or not.

In the above mentioned diagnosing apparatus displaying the ultrasonic three-dimensional image, the living body is scanned with the ultrasonic wave in a three-dimensional manner. In Japanese Patent Application Laid-open Publication Kokai Hei 2-265536, there is disclosed an ultrasonic diagnosing apparatus. As shown in FIG. 1, within an ultrasonic probe 101, an ultrasonic vibrating element 102 is rotated by means of a shaft 103 to effect the radial scan, and at the same time the ultrasonic vibrating element 102 is linearly moved in a direction parallel with a longitudinal axis of the ultrasonic probe 101 to perform a linear scan. In this manner, a cavity wall 104 is scanned spirally with the ultrasonic wave and echo data of a three-dimensional region is obtained.

In this known ultrasonic image diagnosing apparatus, the radial scan and linear scan are carried out in synchronism with each other, so that although the scanning speed is changed, a relative speed of these two scans is not changed, and therefore the three-dimensional ultrasonic image can be obtained always under the same condition.

However, the inventors have found that this known apparatus could be further improved in the following points. That is, in order to obtain a useful three-dimensional ultrasonic image for diagnosis, it is necessary to confirm by the radial scan whether or not a desired area of the cavity wall could be actually observed in the three-dimensional image prior to picking-up the echo data of the three-dimensional region. However, in case of performing this confirmation, when a region of interest (ROI) or a desired area 105 to be diagnosed is positioned near an edge of a three-dimensional scan range as illustrated in FIG. 1, only a portion of the desired area 105 denoted by hatchings can be observed. Moreover, even if an operator can operate the ultrasonic probe such that the desired area 105 is correctly positioned at an origin of the linear scan, i.e. a distal end of the ultrasonic probe 101, it is not always possible to obtain a three-dimensional ultrasonic image including the desired area 105, because the origin of the three-dimensional scan is situated at an edge of the scanning range.

In order to avoid the above problem, one might consider to operate manually the ultrasonic probe 1 such that the desired region, i.e. a region of interest 105 is positioned at about a middle point of the linear scan range. However, in this case, a movement of the ultrasonic probe 101 has to be presumed and thus the operation becomes very cumbersome. Moreover, it can not be guaranteed that the region of interest 105 is positively included in the scanning range. It is further considered that once a three-dimensional image has been constructed to confirm that the region of interest is contained in the image, the picking-up or storing of the echo data is initiated. In this case, the construction of the three-dimensional image requires a long time, so that the confirmation also requires a long time.

SUMMARY OF THE INVENTION

The present invention has for its object to provide a novel and useful ultrasonic image diagnosing apparatus, in which a three-dimensional image of a living body can be obtained accurately within a short time period, while a tonal property of the echo data which is inherent to the living body can be maintained so that useful information for diagnosis can be obtained.

It is another object of the invention to provide a novel and useful ultrasonic image diagnosing apparatus, in which it is possible to confirm whether or not the echo data from the three-dimensional region is suitable for the diagnosis immediately after picking-up or storing the echo data.

It is still another object of the invention to provide a novel and useful ultrasonic image diagnosing apparatus, in which a three-dimensional image of a region of interest of a living body can be simply and promptly obtained.

According to the invention, an ultrasonic image diagnosing apparatus comprises:

an ultrasonic probe means for emitting an ultrasonic wave toward a living body in a three-dimensional manner and receiving an ultrasonic wave reflected by the living body to derive echo data of three-dimensional region;

a three-dimensional data storing means for storing said echo data of three-dimensional region derived from the ultrasonic probe means;

a cross sectional position setting means for setting a desired cross sectional position within the echo data to determine a display range of the echo data of three-dimensional region;

a cross sectional position storing means for storing data representing said cross sectional point set by said cross sectional position setting means;

a surface position extracting means for extracting surface position data representing a surface of an object under inspection from the echo data of three-dimensional region;

a surface position data storing means for storing said surface position data of surface;

a three-dimensional image data producing means for producing three-dimensional image data by converting the echo data within the three-dimensional display range at the cross sectional position set by said cross sectional position setting means into two-dimensional perspective image data seen from a given direction;

a shade adding means for adding shade to a surface of the object to derive surface image data, said surface being indicated by said surface position data;

a surface composing means for producing composed three-dimensional image data by composing said three-dimensional image data formed by said three-dimensional image data producing means and the surface image data having the shade added thereto, at a position corresponding to said extracted surface position; and a display means for receiving said composed three-dimensional image data to display a three-dimensional image.

In the ultrasonic image diagnosing apparatus according to the invention, a desired cross sectional position within the echo data of three-dimensional region is determined by the cross sectional position setting means on the basis of the echo data of three-dimensional region, and then a position of a desired surface of the object to be observed is extracted by the surface position extracting means. The echo data within the desired display region at the determined cross sectional position is converted by the three-dimensional image data producing means into the two-dimensional perspective image data which is seen from a given direction. The extracted surface image data is add with the shade and the thus treated surface image data is composed with the two-dimensional perspective image data to derive the composed three-dimensional image data. Finally, the thus obtained composed three-dimensional image data is supplied to the display means and the three-dimensional image is displayed, in which the surface is added with the desired shade and the cross sectional image has the tonal property inherent to the echo data.

In a preferable embodiment of the apparatus according to the invention, said ultrasonic probe comprises an ultrasonic vibrating element which emits an ultrasonic wave and is arranged at a distal end of an insertion section of an endoscope to be inserted into a cavity of a living body and further includes a first driving means for driving the ultrasonic vibrating element such that a first cross section is scanned by the ultrasonic wave and a second driving means for driving the ultrasonic element such that a second cross section perpendicular to the first cross section is scanned by the ultrasonic wave. The apparatus further comprises a first image data producing means for producing first image data representing a first ultrasonic tomographic image by processing the echo data which is obtained during the scanning in the first cross section, a second cross sectional position setting means for setting a desired cross sectional position in the first ultrasonic tomographic image displayed on the display means, and a second image data producing means for producing second image data representing a second ultrasonic tomographic image at the cross sectional position determined by said second cross sectional position setting means, while the echo data of three-dimensional region is derived by scanning the first and second cross sections.

In this preferable embodiment, after the cross sectional position has been set by watching the first ultrasonic tomographic image, the three-dimensional scan is performed, and during this three-dimensional scan the second ultrasonic tomographic image at said cross sectional position is displayed. Therefore, it can be accurately and promptly whether the echo data of three-dimensional region obtained by the three-dimensional scan is suitable for diagnosis or not.

Another preferable embodiment of the ultrasonic image diagnosing apparatus according to the invention comprises a means for generating an image pick-up start signal for initiating a storing of the echo data of three-dimensional region, and a control means for controlling said first and second driving means such that prior to the generation of said image pick-up start signal, only the scan on the first cross section by the first driving means is performed at a given position with a scanning range on said second cross section except of both ends thereof, and after the generation of said image pick-up start signal, the three-dimension scan is performed by said first and second driving means and the echo data of three-dimensional region is stored. In this case, it is preferable that the first scan is effected by the radial or sector scan and the second scan is performed by the linear scan.

In this embodiment, prior to storing of the echo data of three-dimensinal region, it is possible to confirm easily and accurately that a region of interest is existent within the linear scanning range by monitoring the B-mode ultrasonic tomographic image due to the radial or sector scan.

According to further aspect of the invention, an ultrasonic image diagnosing apparatus for effecting emission and reception of an utlrasonic wave with respect to a living body, picking-up echo data of three dimensional region, and displaying an ultrasonic image within the living body by processing the picked-up echo data comprises:

- a three-dimensional data storing means for storing said echo data of three-dimensional region;
- a cross sectional position setting means for setting a desired cross sectional position within said echo data of three-dimensional region;
- a surface position extracting means for extracting a desired position of a surface of an object within the echo data of three-dimensional region;
- a surface position storing means for storing the extracted surface position data;
- an inside data storing means for storing three-dimensional data within the living body except for said extracted surface;
- a shading means for effecting a shading treatment upon a surface which is denoted by surface position data stored in said surface position storing means;
- an image composing means for composing the surface image data with the applied shade and the three-dimensional image data to produce composed image data;
- a data cutting means for cutting the surface position data and said inside data or said composed image data at said cross sectional position set by said cross sectional position setting means; and
- a display means for converting said composed image data into two dimensional projection data to display a three-dimensional image.

According to still another aspect of the invention, an ultrasonic image diagnosing apparatus for performing a three-dimensional scan by driving an ultrasonic vibrating element by performing first and second scans on first and second cross sections by means of first and second driving means, respectively to obtain a three-dimensional ultrasonic image, comprises:

- an image pick-up start signal generating means for generating an image pick-up start signal for initiating the pick-up of echo data of three-dimensional region; and
- a control means for controlling said first and second driving means such that prior to the generation of said image pick-up start signal, only a scan on said first cross section is performed by said first driving means at a position within a scanning range on said second cross section except for its both ends, and after the generation of said image pick-up start signal, the echo data of three-dimensional region is stored.

BRIEF DESCRIPTION OF THE DRAWINGS

FIG. 4 is a schematic view explaining the image processing operation;

FIGS. 5A and 5B are perspective views illustrating the image processing operation in a second embodiment of the ultrasonic image diagnosing apparatus according to the invention;

FIG. 6 is a schematic view showing a displayed image for explaining the image processing operation in a third embodiment of the ultrasonic image diagnosing apparatus according to the invention;

FIGS. 8A and 8B are schematic views illustrating the processed images in the fourth embodiment;

FIG. 9 is a flow chart denoting the image processing operation in a fifth embodiment of the ultrasonic image diagnosing apparatus according to the invention;

FIG. 10 is a diagram showing coordinates in a memory space corresponding to the three-dimensional data;

FIGS. 11A and 11B are ultrasonic tomographic images on which a marker for indicating a region of interest;

FIG. 12 is a schematic view showing a relationship between a plurality of tomographic images and the marker position;

FIG. 13A is a tomographic image and FIG. 13B shows the change in the cross sectional images;

FIG. 14 is a perspective view illustrating the ultrasonic probe;

FIG. 15 is a cross sectional view showing an embodiment of the device for driving the ultrasonic vibrating element according to the invention;

FIG. 17 is a cross sectional view showing another embodiment of the ultrasonic vibrating element driving device according to the invention;

FIG. 18 is a circuit diagram illustrating a part of the device of FIG. 17; and

FIG. 19 is a perspective view illustrating still another embodiment of the ultrasonic vibrating element driving device according to the invention.

DESCRIPTION OF THE PREFERRED EMBODIMENTS

Figure 1:
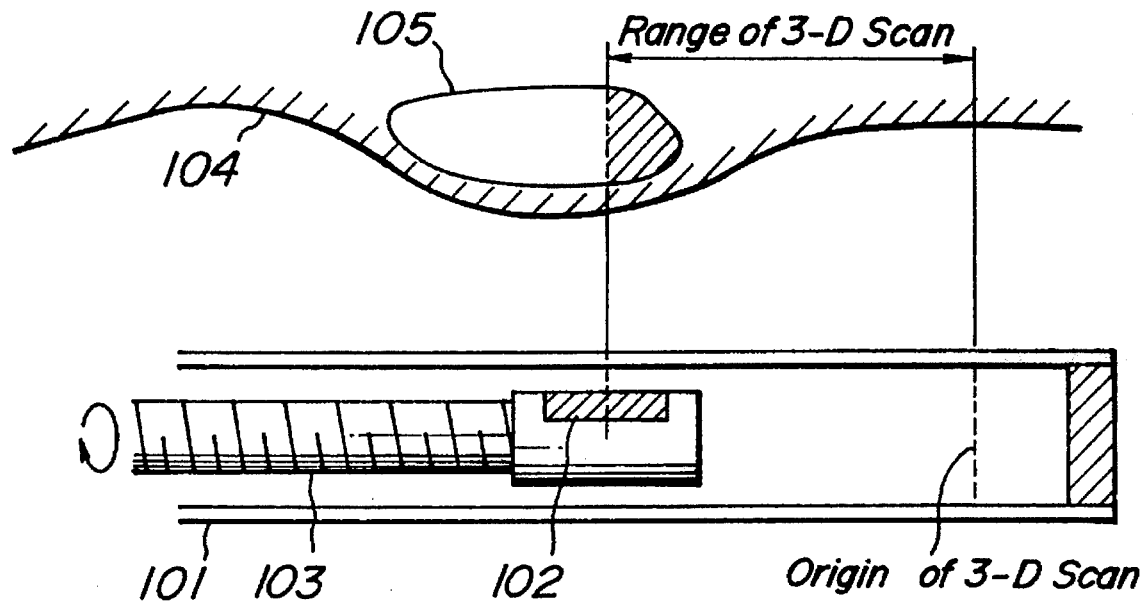
FIG. 1 is a schematic view for explaining the operation of the three-dimensional scanning in the known ultrasonic image diagnosing apparatus.
Figure 2:
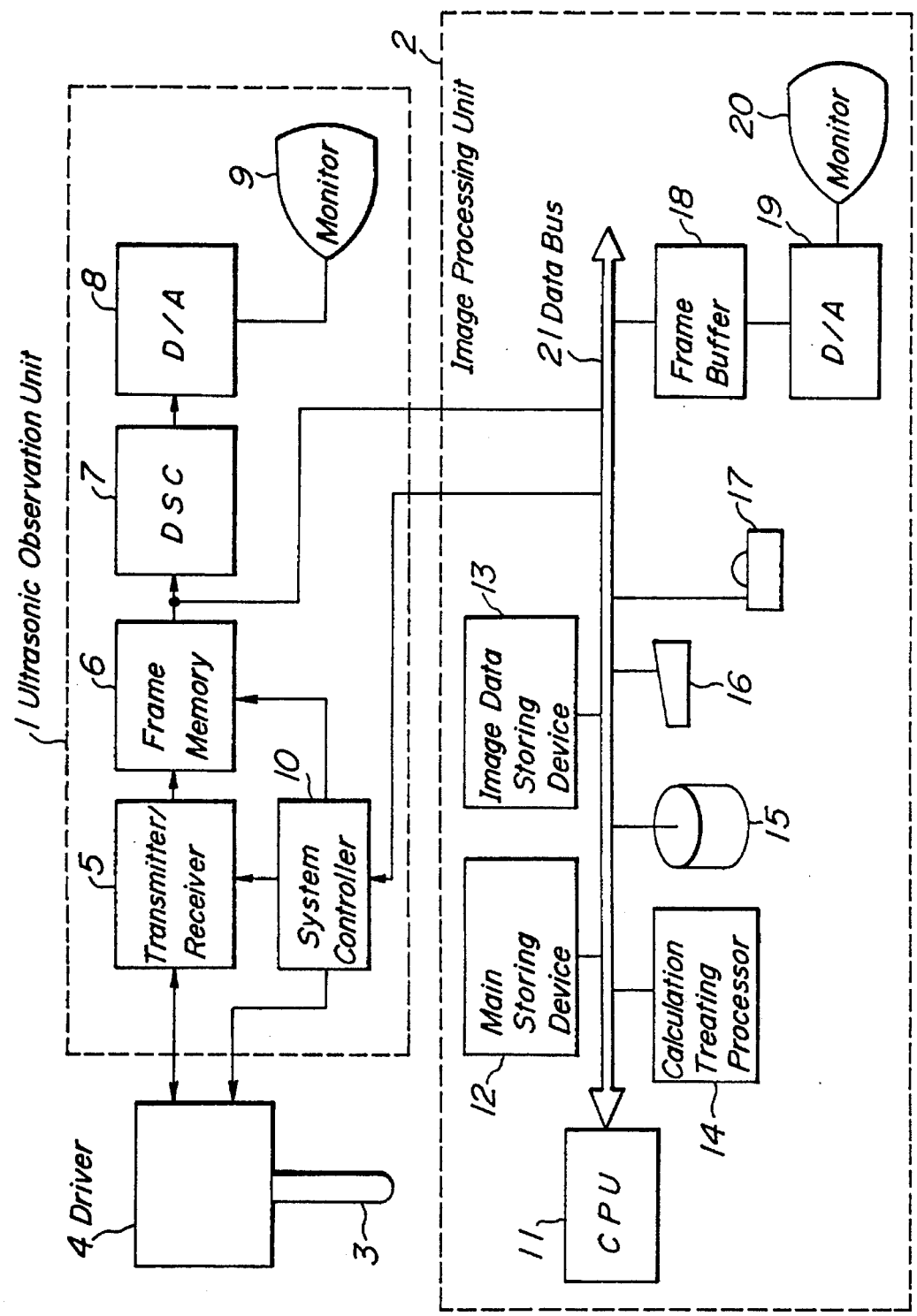
FIG. 2 is a block diagram showing a general construction of a first embodiment of the ultrasonic image diagnosing apparatus according to the invention.
Figure 3:
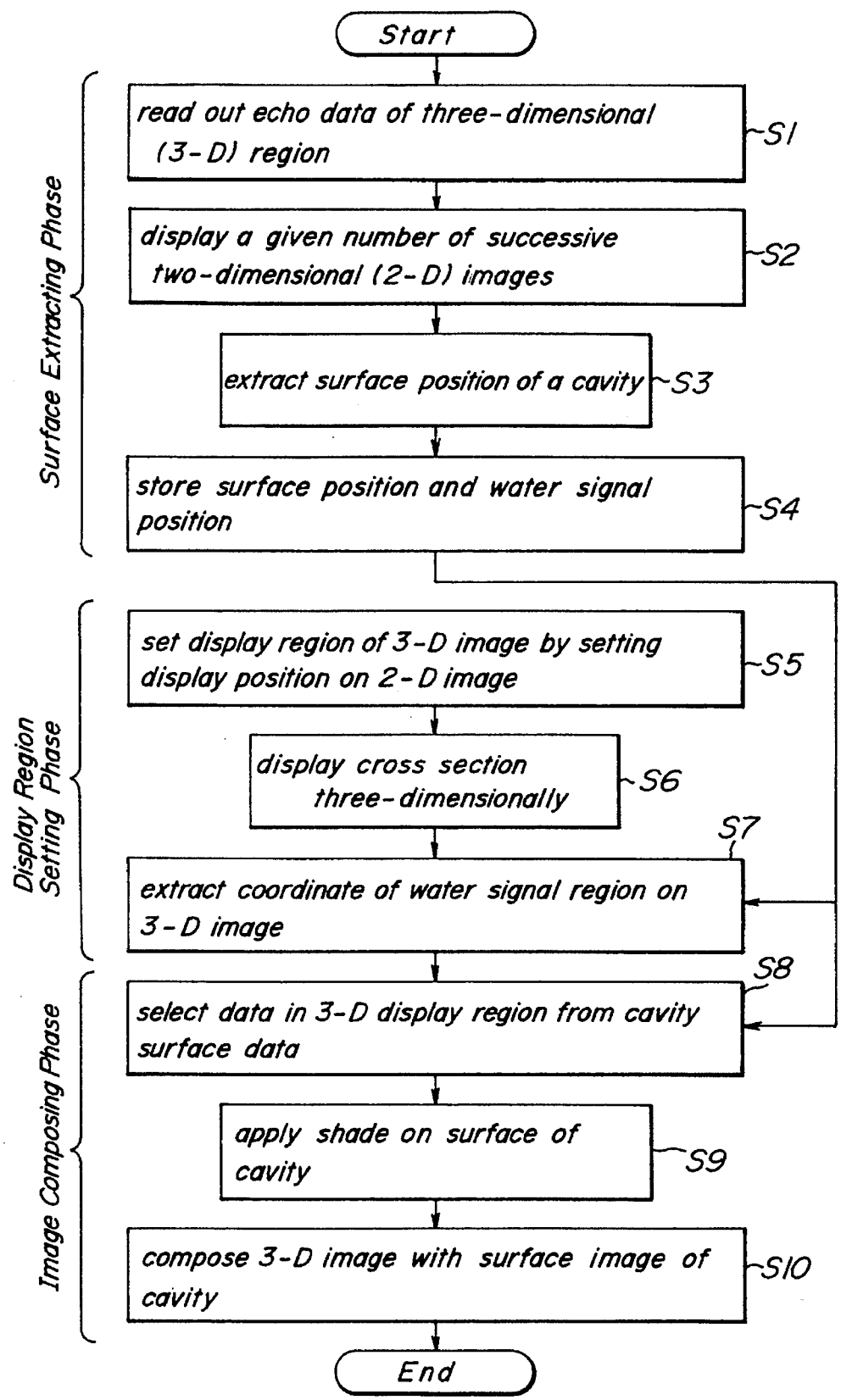
FIG. 3 is a flow chart representing the operation of the apparatus shown in FIG. 2.

FIGS. 2 to 4 show a first embodiment of the ultrasonic image diagnosing apparatus according to the invention. FIG. 2 is a block diagram showing a whole construction of the apparatus, FIG. 3 is a flow chart representing the image processing operation and FIG. 4 is a schematic diagram explaining the image processing operation.

As shown in FIG. 2, the ultrasonic image diagnosing apparatus according to the invention comprises an ultrasonic observation unit 1 which transmits and receives an ultrasonic wave and displays an ultrasonic image in a real time mode, and an image processing unit 2 which performs image processing upon echo data derived from the ultrasonic observation·unit 1 in order to display a three-dimensional image. To the ultrasonic observation unit 1 are connected an ultrasonic probe 3 including an ultrasonic vibrating element or transducer and a driver 4 driving the ultrasonic probe 3.

The ultrasonic observation unit 1 comprises transmitter/receiver 5 for transmitting the ultrasonic wave toward a living body under inspection and receiving an echo signal representing an ultrasonic wave reflected by the living body to produce the echo data, frame memory 6 storing the echo data, digital scan converter (DSC) 7 converting the echo data stored in the frame memory 6 into a television image signal composed of successive scanning lines, D/A converter 8 converting the digital television image signal into an analog television image signal, monitor 9 displaying an echo image in a real time mode in accordance with the image signal derived from the D/A converter 8, and system controller 10 controlling the operation of the driver 4, transmitter/receiver 5 and frame memory 6.

Upon performing the ultrasonic observation, the ultrasonic probe 3 is inserted into a cavity of the living body, and then the transmitter/receiver 5 and driver 4 are controlled by the system controller 10 such that the ultrasonic vibrating element provided in the distal end of the probe 3 is driven radially as well as linearly to scan the cavity in a three-dimensional manner while ultrasonic pulses are transmitted from the ultrasonic vibrating element. In this manner, echo data from a three-dimensional region within the cavity is stored in the frame memory 6. The thus obtained echo data of a three-dimensional region is processed by the DSC 7 and D/A 8 and an echo image is displayed on the monitor 9 as an ultrasonic observation image. At the same time, the echo data is supplied from DSC 7 or frame memory 6 to the image processing unit 2 in the form of a plurality of mutually parallel two-dimensional cross sectional images. It should be noted that additional data such as a size of the two-dimensional image and a distance between successive two-dimensional cross sectional images is also supplied from the ultrasonic observation unit 1 to the image processing unit 2.

The image processing unit 2 comprises CPU 11 for controlling the image processing operation, main storing device 12 for storing data obtained by the image processing, image data storing device 13 used as the three-dimensional image data storing means for the image data supplied from the ultrasonic observation unit 1, calculation treating processor 14 for performing at a high speed various operations such as surface extracting treatment, shading treatment, surface composing treatment and projection converting treatment, external storing device 15 for storing information such as various programs and back-up data, operation terminal 16 in the form of a keyboard, track ball 17 used as a cross sectional position setting means for setting an image display area, frame buffer 18 for temporarily storing processed image data, D/A converter 19 for converting the digital image data into analog image data and monitor 20 for displaying a three-dimensional image. The above mentioned various components are connected to each other via a data transmission bus 21.

The image data and additional data sent to the image processing unit 2 are stored in the image data storing device 13 as a plurality of two-dimensional ultrasonic tomographic images in the order in which the image data is picked-up. The calculation treating processor 14 performs the surface extracting treatment, shading treatment, surface composing treatment and projection converting treatment on the basis of the image data and additional data stored in the image data storing device 13 to derive the three-dimensional image data. The thus derived three-dimensional image data is supplied to frame buffer 18 and is stored therein temporarily. Then, the three-dimensional image data is supplied to the monitor 20 by means of D/A converter 19. In this manner, the three-dimensional ultrasonic image can be displayed on the two-dimensional display screen of the monitor 20.

The operation of the calculation treating processor 14 is controlled by CPU 11 such that the above mentioned various treatments are carried out. Now the image processing procedure performed by the CPU 11 and processor 14 will be explained in detail with reference to a flow chart shown in FIG. 3 as well as to a schematic view illustrated in FIG. 4.

As shown in FIG. 3, the image processing procedure may be classified into three phases, i.e. surface extracting phase, display region setting phase and image composing phase.

During the surface extracting phase, in a step S1, the echo data of a three-dimensional region (three-dimensional data) is read out of the image data storing device 13 together with the additional data. In a next step S2, a plurality of successive two-dimensional ultrasonic cross sectional images or ultrasonic tomographic images are displayed as denoted by a reference numeral 32 in FIG. 4, the number of which may be set by means of the keyboard 16.

Next, in a step S3, a position of a surface of a cavity under inspection is extracted by removing a water signal representing not only water but also blood and humor contained in the cavity from a displayed two-dimensional cross sectional image as illustrated by 33 in FIG. 4. The water signal has a lower value than the cavity surface signal, and thus the water signal may be simply removed by setting a suitable threshold level. In this manner, a position of the surface of the cavity can be extracted. This process is carried out for all the cross sectional images to derive the position of the entire surface of a portion of the cavity under inspection. Then, in a step S4, the thus extracted position of the surface of the cavity and the position of the water signal are stored in the main storing device 12.

Next, in a step S5, a desired two-dimensional image selected by an operator is displayed, and straight lines 34a and 34b are moved on the displayed two-dimensional image by operating the track ball 17 as depicted by 35 in FIG. 4. During this step, a desired position of a cross section perpendicular to the displayed two-dimensional image may be set. In this manner, it is possible to set a three-dimensional region to be displayed on the monitor 20.

In a step S6, after the two-dimensional image data within the thus set three-dimensional region has been interpolated to obtain continuous data as shown by 36 in FIG. 4, a desired viewing direction is set by operating the track ball 17. Then, the two-dimensional projection conversion in the thus set viewing direction is performed (affin transformation and hidden surface removal processing) to provide a three-dimensional image signal. In this case, a three-dimensional effect is enhanced by performing the Gouraud shading to such an extent that the tonal characteristic in the echo image of the cross sections of the cavity within the display region to the object information is not lost.

Next, in a step S7, from the data of the water signal extracted in the step S3 is selected only a part of the data within the three-dimensional display region as depicted by 37A in FIG. 4. Then, the selected data is interpolated to obtain continuous data. After that, the two-dimensional projection conversion is carried out as shown by 37B in FIG. 4 in a similar manner in the step S6. In this manner, coordinates of the water signal region in the three-dimensional image denoted by hatching are extracted as indicated by 37C.

In a next step S8, from the data of the surface of the cavity extracted in the step S3, only that part thereof which is in the three-dimensional display region set in the step S5 is selected as illustrated by 38 in FIG. 4, and the thus selected data is subjected to interpolation to obtain continuous data.

In a step S9, the surface data of the cavity selected in the step S8 is converted into a three-dimensional model by a surface model method, and further the two-dimensional projection conversion and Gouraud shading are performed for the surface of the cavity as indicated by 39 in FIG. 4 similar to the step S6.

In a final step S10, the three-dimensional image obtained by the step S6 and the cavity surface image processed by the step S9 are composed as depicted by 40 in FIG. 4.

In the manner explained above, in the present embodiment, the three-dimensional image of the cross section of the cavity having the tonal characteristic based on the object information inherent to the echo data can be composed with the three-dimensional image of the surface of the cavity which has been processed by the three-dimensional display and Gouraud shading by using the surface model method to produce the three-dimensional ultrasonic image of the region of interest of the object, and the thus produced image is displayed on the monitor 20 by means of the frame buffer 18 and D/A converter 19.

In the present embodiment, the image of the surface of the cavity obtained by performing the extraction of the position of the surface of the cavity, the three-dimensional display using the surface model method and the shading treatment, and the cavity cross sectional image displayed three-dimensionally in accordance with the tonal characteristic based on the object information inherent to the echo data are composed with each other to display the accurate three-dimensional image of the cavity within a short time period, said three-dimensional image of the cavity being useful for diagnosis. That is to say, according to the invention, the three-dimensional display can be carried out by treating only the bivalent data of the surface with the aid of the surface model method and on the cross section of the cavity, the three-dimensional display is effected on the basis of the tonal characteristic, so that a required time period for image processing can be shortened and the good three-dimensional image can be displayed without losing the tonal characteristic based on the object information in the echo data.

Furthermore, the surface of the cavity is treated separately from the cross section, and therefore the surface may be provided with any desired shading. Therefore, the cross sectional image can be easily seen without deteriorating the recognizing faculty for multi-layer construction. Moreover, the cross sectional image may be subjected to the shading treatment separately from the surface of the cavity. It is possible to display a good image having a sufficient tonal characteristic for the diagnosis.

Also in the present embodiment, the position of the cross section, i.e. the region of the three-dimensional display, may be simply but precisely set by means of the track ball 17. Therefore, the setting time period is very short.

In the present embodiment, the surface of the cavity is extracted by removing the water signal, but the surface may be equally extracted even for the blood or humor.

In the step S6, the cross sectional image is subjected to the shading process, but this shading process may be dispensed with.

Moreover, in the present embodiment, the ultrasonic vibrating element is arranged in the distal end of the insertion section of the endoscope which is inserted into the cavity, but according to the invention, the ultrasonic vibrating element may be provided on a unit which is brought into contact with an outer surface of a living body.

In the present embodiment shown in FIG. 2, the image data to be supplied to the image processing unit 2 is derived from the output of DSC 7, but according to the invention, it may be derived from the output of the frame memory 6 in the form of data along a desired sound line. Furthermore, the image data storing device 13 is provided in addition to the main storing device 12, but they may be constructed by a single storing device.

The results obtained by each of the steps in the flow chart shown in FIG. 3 may be stored in either one or both of the main storing device and the image data storing device. That is to say, the main storing device and/or image data storing device may serve as the three-dimensional data storing means, cross sectional position storing means and surface position storing means.

As stated above, in the present embodiment, the cavity surface is converted into the three-dimensional model by means of the surface model method. It should be noted that method, according to the invention any other method such as a solid model method may be equally utilized.

Further, the shading treatment is performed by the Gouraud shading, but any other methods such as flat shading, horn shading and dip skew (shading in a depth direction perpendicular to the display surface) may be utilized solely or in combination.

FIGS. 5A and 5B are schematic views illustrating the image processing in a second embodiment of the ultrasonic image diagnosing apparatus according to the invention. In this second embodiment, the step S6 for setting the three-dimensional region denoted by 36 in FIG. 4 and the step S7 for extracting the coordinates of the water signal shown by 37B in FIG. 4 are modified. The remaining construction is entirely identical with the previous embodiment and thus is not explained here.

In the second embodiment, as shown in FIG. 5A, only the lowermost plane is displayed over its whole region by ignoring the three-dimensional display region set by the step S5 only for the lowermost plane, i.e. the lowermost tomographic image. Therefore, the data for indicating the position of the water signal is also changed as illustrated in FIG. 5B. The remaining steps are identical with those of the previous embodiment.

In this embodiment, the three-dimensional image seen in the viewing direction directed downward contains the whole area of the lowermost plane, and thus the positional relation can be grasped much more easily so that the diagnosis becomes easy.

It should be noted that if a three-dimensional image seen in a viewing direction directed upward is displayed, only the uppermost plane may be displayed over its whole area.

FIG. 6 is a schematic view showing the image processing in a third embodiment of the ultrasonic image diagnosing apparatus according to the invention.

In this third embodiment, the step S10 in the first embodiment for composing the images is modified. That it to say, the display screen of the monitor is divided into four sections and in one of these sections (left upper section) there is displayed the three-dimensional image which is the same as that of the second embodiment, and in the remaining three sections there are displayed two-dimensional cross sectional images Ap, Bp and Cp which are formed by interpolating image data on cross sections denoted by A, B and C, respectively in the three-dimensional image. Further cross lines 30 of these cross sections are displayed.

The position of the cross section lines 30 displayed on the two-dimensional images Ap, Bp and Cp can be moved by operating the track ball 17. It should be noted that when the cross section lines 30 are moved, the cross sectional position of the three-dimensional image can be also changed. In this manner, the cross sectional position of the three-dimensional image and two-dimensional images can be changed easily and accurately in an interactive manner.

As stated above, in the present embodiment, instead of the step S5 in FIG. 3, the display region is set by moving the cross sectional lines by operating the track ball 17, and then the steps S6 to S10 are performed. By repeating this process, the position of the cross section can be changed.

In the third embodiment, in addition to the three-dimensional image, the two-dimensional cross sectional images are displayed on the monitor, so that the diagnosis may be carried out much more accurately by considering the cross sectional position setting treatment, hidden surface removal treatment and a portion which is removed by the threshold processing.

In the third embodiment, the lowermost plane and mutually orthogonal side planes A, B and C are displayed, but according to the invention the cross sectional image on the uppermost plane may be displayed instead of one of the above four cross sectional images.

Furthermore, the position of the cross section is changed by moving the cross sectional lines on the two-dimensional images, but according to the invention the cross sectional position may be changed by moving cross sectional lines displayed on the three-dimensional image.

Figure 7:
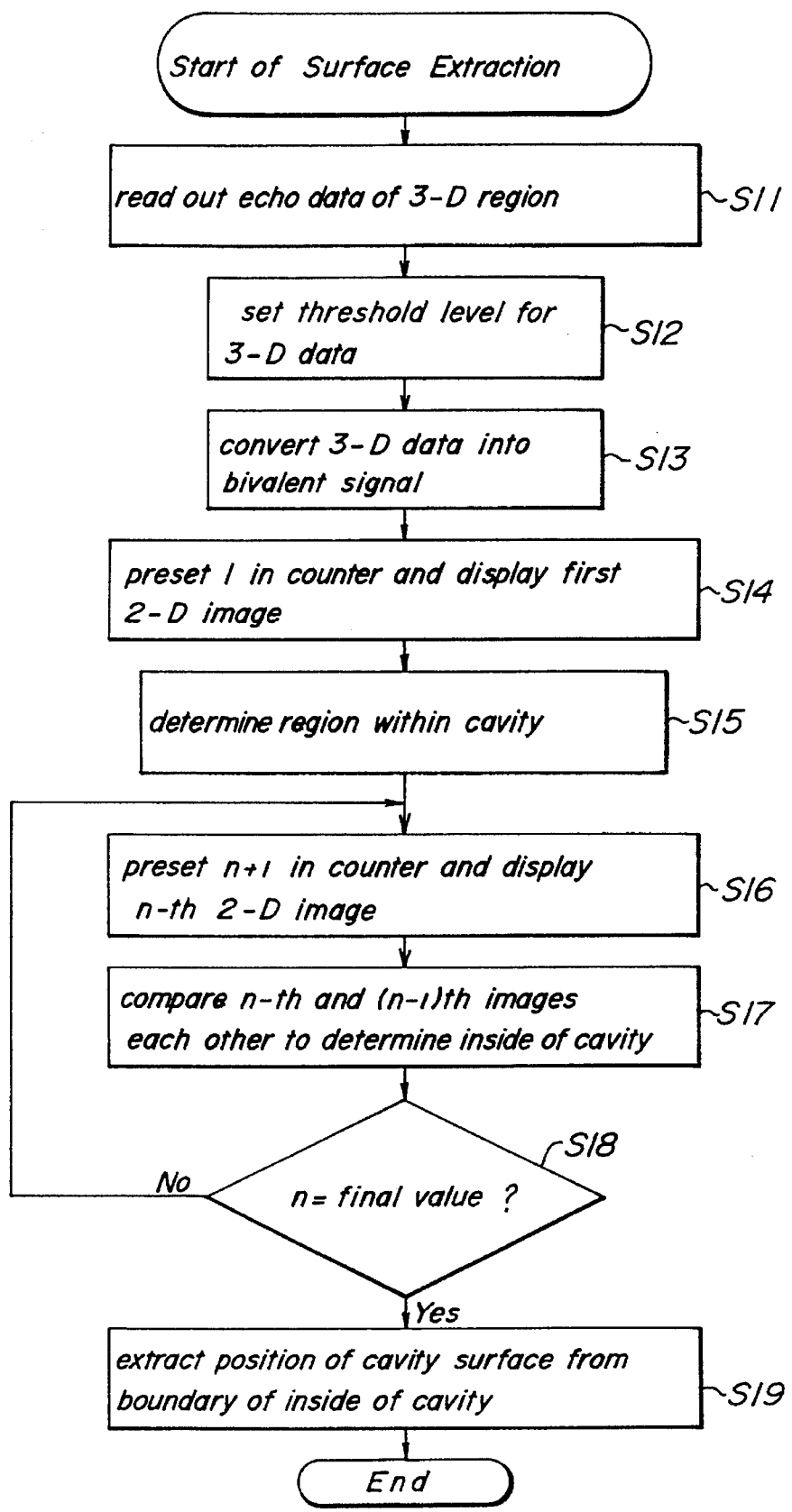
FIG. 7 is a flow chart representing image processing steps in a fourth embodiment of the ultrasonic image diagnosing apparatus according to the invention.

FIG. 7 is a flow chart and FIGS. 8A and 8B are schematic views showing the image processing in a fourth embodiment of the ultrasonic image diagnosing apparatus according to the present invention.

In the fourth embodiment, the surface extracting step in the first embodiment is modified. The flow chart shown in FIG. 7 represents only the surface extracting process. In a step Sll, the echo data of a three-dimensional region is read out of the image data storing device 13 together with the additional data, and in a step S12, a suitable threshold level is set for the echo data. In the present embodiment, during this step S12, successive two-dimensional images, i.e. B-mode ultrasonic tomographic images, are displayed on the monitor 20 as shown by 32 in FIG. 4. Therefore, the operator can set the threshold level by operating the keyboard 16 or track ball 17 while the displayed B-mode ultrasonic tomographic images are monitored. That is to say, the B-mode image displayed on the monitor 20 is converted into the bivalent signal in accordance with the threshold level, so that by changing the threshold level, contents of tomographic images are changed. Therefore, the threshold level may be set such that the surface of the cavity can be clearly seen.

In a step S13, the three-dimensional data is read out of the image data storing device 13 and is converted into bivalent data by using the threshold level set by the step S12.

Next, in a step S14, the calculation treating processor 14 presets a count value n of 1 in its counter, and a first cross sectional image (bivalent B-mode tomographic image) among a plurality of cross sectional images is displayed on the monitor 20 as shown in FIG. 8A. In FIG. 8A, hatched regions correspond to portions having low echo. A region A represents a portion which is filled with water, and regions B and C are located in a region of interest, but due to the bivalent treatment, its brightness is lost. The operator may indicate with the aid of the keyboard 16 or track ball 17 that a point on the region A is within the cavity.

In a step S15, the processor 14 determines a whole region within the cavity by recognizing a fact that adjacent pixels having the same low echo as that of the point set in the step S14 are positioned within the cavity. In this manner, the position of the inside of the cavity is determined for the first tomographic image.

Next, in a step S16, n+1 is preset in the counter in the processor 14 and an n-th B-mode tomographic image is displayed as shown in FIG. 8B. Then, in a step S17, the processor 14 compares the n-th image and (n−1)th image with each other. In this case, low echo portions An and Bn in the n-th image have portions which are superimposed upon the portion An-1 in the (n−1)th image which has been recognized to be within the cavity. Usually, the region within the cavity has a most large area among low echo portions, so that in the present embodiment, the largest overlapping region An is recognized as the region within the cavity.

Next, in a step S18, the processor 14 checks whether the count value in the counter has reached the final value or not. When the count value does not reach the final value, the process is returned to the step S16 and repeats the steps 16 and 17. On the other hand, when the count value has arrived at the final value, the process advances to a step S19. In the step S19, the position of the surface of the cavity is extracted as boundaries between the cavity and the inside of the cavity for respective tomographic images.

After the position of the cavity surface has been extracted by the method mentioned above, the setting of the display region and image composing are preformed in the same manner as those of the first embodiment. In the present embodiment, the position of the inside of the cavity, i.e. the position of the water signal, can be extracted automatically by merely indicating the point in the inside of the cavity on the first B-mode tomographic image, so that the extraction of the surface of the cavity can be carried out much more accurately. It should be noted that upon picking-up the three-dimensional data, distances between successive image data in the spatial domain as well as in the time domain is very small. Therefore, a shift of the inside of cavity between successive images is very small, and thus the position of the boundary between the inside of the cavity and the surface of the cavity can be detected precisely.

Now several modifications of this fourth embodiment will be explained. In the step S17, the inside of the cavity is determined to be the largest region among the low echo portions An and Bn which are superimposed on the inside region An-1, but a region having an area which is closest to the area of the inside region An-1 may be determined as the inside of the cavity.

Further, in the step 15, the inside of the cavity on the first cross-sectional image is set by the operator by means of the keyboard 16 or track ball 17, but this may be automatically performed. For instance, a lower echo portion having the largest area may be determined as the inside of the cavity.

Moreover, after the determination of the inside of the cavity has been completed for all the two-dimensional images in the steps S16 and S17, the surface of the cavity is extracted as the boundary of the inside of the cavity, but after an inside of cavity is determined for a two-dimensional image, a surface of the cavity may be extracted.

Furthermore, the point within the inside of the cavity is set by the operator for the first tomographic image, but this may be performed on any desired tomographic image which clearly indicates the position of the inside of the cavity.

In the step S13, the echo data is subjected to the bivalent treatment as the threshold treatment, but according to the invention, other threshold treatment may be carried out. For instance, pixels having brightnesses which are lower than the threshold level may be removed.

FIG. 9 is a flow chart showing the image processing in a fifth embodiment of the ultrasonic image diagnosing apparatus according to the invention, and FIG. 10 is a schematic view illustrating spatial coordinates in the memory corresponding to the picked-up three-dimensional data.

In this embodiment, the data representing the position of the surface of the cavity and the data representing a wall or bulk of the cavity are stored separately. The processor 14 performs the data cut treatment, shading treatment, image composing treatment and projection converting treatment at a high speed.

Parts of the main storing device 12, image data storing device 13 and external storing device 15 are utilized for storing the surface position data and other parts thereof are used to store the cavity bulk data. In this case, memory spaces of respective storing devices are treated as a space having a unit volume (vowel space) corresponding to orthogonal coordinates set in the three-dimensional space. Then, each of the picture elements or voxels are denoted by three parameters (x, y, z) as shown in FIG. 10.

At first, in a step S21, the echo data stored in the image data storing device 13 is read out together with the additional data, and in a step S22, a given number of successive two-dimensional images or ultrasonic tomographic images are displayed, this number being set by the keyboard 16. Then, in a step S23, the water signal within the cavity is removed from these tomographic images to extract the position of the surface of the cavity. It should be noted that the extraction of the position of the surface of the cavity may be carried out by the method used in the fourth embodiment.

In a step S24, for voxels within the surface position data storing means corresponding to the position of the surface of the cavity, data '1' is set and remaining voxels are assigned with data '0'.

At the same time, in a step S25, voxels within the cavity bulk data storing means corresponding to the bulk of the cavity wall are given with respective echo data.

In these steps S24 and S25, the surface position data and cavity bulk data are stored in respective memory means.

Next, in a step S26, the operator sets a suitable plane for monitoring a cross sectional image of the cavity with the aid of the keyboard 16 or track ball 17. In this manner, the cross sectional position of the three-dimensional display region has been set.

Then, in a step S27, the surface position data and cavity bulk data stored in the steps S24 and S25 are cut in accordance with the cross sectional position set in the step S26. In the present embodiment, all voxels positioned on one side of the cross section cut at the cross sectional position set by the step S26 are given with '0'. Similar treatment is performed for the cavity bulk data.

In a step S28, the surface position data is subjected to the shading process. For instance, respective voxel data in the surface position data storing device is weighted in accordance with shade which reflects distances from an imaginary light source, directions of light rays and shape of the surface. Products of the values '1' or '0' of respective voxels and weights are derived and the thus derived products are set to respective voxels instead of the data values '1' or '0'.

Next, in a step S29, corresponding voxels in the surface position data storing means and bulk data storing means are summed to derive composed data of the surface position data and cavity bulk data. In this manner, it is possible to produce the three-dimensional image having the data of the surface of the cavity with shade and the data of the cross section of the cavity having contrast which is inherent to the object information.

Finally, in a step S30, the composed data obtained by the step S29 is subjected to the hidden surface removal treatment and two-dimensional projection treatment and the thus treated image data is displayed on the monitor.

Also in the present embodiment, the displayed three-dimensional image has the cavity surface having shade added thereto and the cavity cross section having contrast inherent to the ultrasonic echo, and therefore the three-dimensional image can be much more easily seen. Further, the data of the cavity surface position and the data of the bulk or wall of the cavity are separately stored and processed from each other, and thus the processing time can be shortened and the position of the cross section may be easily changed to obtain a desired three-dimensional image promptly.

Furthermore, by utilizing the image process of the present embodiment, it is possible to inspect not only the cavity of a living body such as stomach, but also the surface and inside of organs within the living body.

In the above embodiment, in the step S27, the data is subjected to the cutting treatment, but according to the invention this cutting treatment may be performed after the image composing step S29. In this case, the change of the cut position can be easily and promptly effected by storing the composed data obtained by the step S29.

In the step S28, the shading treatment is carried out by deriving the products of the voxel data '1' or '0' and the weights, but the shading treatment may be performed by deriving sums thereof in addition to the products.

In the step S28, the shading treatment is carried out only on the voxels corresponding to the surface position of the cavity, but according to the invention, the inside voxels may be also subjected to the shading treatment.

In the above explained embodiments, the storing of the echo data of the three-dimensional region requires a substantial time, so that it might be affected by a movement of the patient. Therefore, it is preferable to check before effecting the image processing whether or not the echo data has been picked-up correctly. Particularly, when the cross section is set to be perpendicular to the plane of the two-dimensional image, there is contained data which extends over a plurality of successive two-dimensional images, so that the image quality of the obtained three-dimensional image is largely affected by the movement of the body.

Now a sixth embodiment of the ultrasonic image diagnosing apparatus according to the invention which can solve the above explained problem will be explained.

FIGS. 11a and 11b are schematic views explaining the method of aligning a region of interest (ROI) with a marker denoting the position of a cross section. FIG. 12 is a schematic diagram showing a positional relation between a plurality of successive two-dimensional images and the position of a cross section. FIGS. 13a and 13b are schematic views explaining a manner of changing the position of cross section, and FIG. 14 is a perspective view of the ultrasonic probe. The whole construction of this sixth embodiment is substantially identical with that of the first embodiment shown in FIG. 2. That is to say, the image data and additional data transmitted to the image processing unit 2 are stored in the image data storing device 13 as a plurality of Successive two-dimensional images in an order in which they are picked-up. The calculation processor 14 processes the image data and additional data to perform the DSC treatment, surface extracting treatment, shading treatment, image composing treatment and projection converting treatment. The thus processed three-dimensional image data is temporarily stored in the frame buffer 18 and then is supplied to the monitor 20 by means of the D/A converter 19. In this manner, the three-dimensional image of the cavity including the ROI can be displayed on the monitor 20.

The image data stored in the image data storing device 13 is read out and ultrasonic tomographic images 71 are displayed on the monitor 20 as illustrated in FIG. 11a. On this image 71 there is also displayed a marker 72 which denotes a sound direction y. Then, the operator rotates the tomographic image 71 by means of the track ball 17 such that a region of interest (ROI) 73 is positioned on the marker line 72 as shown in FIG. 11b. It should be noted that the above process has to be performed before picking-up the echo data of a three-dimensional region. Furthermore, the data of the tomographic image 71 is processed in the form of the sound line, so that the rotation of the tomographic image can be simply effected by merely changing a pickup position of the sound line during the DSC treatment.

Next the method of displaying the three-dimensional image by processing the echo data of the three-dimensional region after the position of the cross section has been determined will be explained.

As illustrated in FIG. 12, during the storing of the echo data of the three-dimensional region, a plurality of successive tomographic images 71 are picked-up and stored in the image data storing device 13. Then, the three-dimensional image is displayed by interpolating the sound line data on the marker 72 to obtain a number of cross sectional images and then these cross sectional images are successively aligned.

As explained above, in the sixth embodiment, the three-dimensional image containing the ROI 73 can be easily and promptly displayed. Even if the ROI 73 is not displayed on the three-dimensional image due to the movement of the body during the picking-up of the data, it is possible to display the three-dimensional image including the ROI 73 by successively displaying cross sectional images a, b and c shown in FIG. 13b, these images being cut along marker lines a, b and c in FIG. 13a. The marker b corresponds to the originally set marker and the markers a and c are shifted in clockwise and anti-clockwise directions, respectively by an angle θ. In FIG. 13b, an arrow indicates that the cross sectional images are successively changed in a cyclic manner. It should be noted that a time period of this change may be adjusted by the track ball 17.

In the sixth embodiment, a plurality of cross sectional images are successively displayed on the same portion of the monitor 20, and thus it is possible to confirm whether the picked-up echo data of the three-dimensional region is correct or not in an easy and prompt manner. Compared with a case in which a plurality of cross sectional images are displayed in divided areas of the monitor screen, the cross sectional image having a large size can be displayed.

In the sixth embodiment, when the ROI 73 is not contained in the displayed three-dimensional image, the cross sectional image is rotated while the marker 72 is set to be stationary. According to the invention, the marker 72 may be rotated with respect to the cross sectional image. Further, in the sixth embodiment, three cross sectional images along the marker lines a, b and c are successively displayed, but according to the invention, the number of these images is not limited to three, but may be determined at will.

In order to derive the echo data of the three-dimensional region, the ultrasonic vibrating element arranged in the distal end of the ultrasonic probe is rotated and moved linearly. According to the invention, a pair of ultrasonic vibrating elements may be arranged in the probe as illustrated in FIG. 14. In this embodiment, rear surfaces of two ultrasonic vibrating elements 75a and 75b are contacted with each other and an assembly is rotated at a constant speed by means of a rotation of a flexible shaft 76 in a direction shown by an arrow. An output signal derived from one of the elements 75a and 75b is delayed for a time which is equal to a half of a period of rotation, and then the thus delayed output signal is summed with a non-delayed output signal from the other element. In this manner, the S/N of the displayed images can be improved.

Next a seventh embodiment of the ultrasonic image diagnosing apparatus according to the invention will be explained. In the sixth embodiment, the three cross sectional images a, b and c corresponding to the marker line 72 and two marker lines shifted from the marker line 72 by ±θ are successively displayed on the monitor. In the seventh embodiment, a plurality of cross sectional images are simultaneously displayed at different areas on the monitor screen. The remaining construction of the seventh embodiment is entirely the same as that of the sixth embodiment. In this seventh embodiment, a plurality of cross sectional images can be seen simultaneously, so that the operator can easily confirm whether the ROI is contained in the picked-up echo data of the three-dimensional region.

As explained above, in the sixth and seventh embodiments of the ultrasonic image diagnosing apparatus according to the invention, prior to the picking-up of the echo data of the three-dimensional region, the position of the desired cross section is set, and a plurality of cross sectional images at the desired cross sectional position as well as in a vicinity thereof immediately after the completion of the picking-up of the echo data. Therefore, the region of interest can be positively contained in the three-dimensional image without being affected by the movement of the patient body, so that the quality of the displayed three-dimensional image can be judged by a simple operation. This results in a shortening of the test time and thus the patient's discomfort can be mitigated.

Now the driving device for driving the ultrasonic vibrating element such that the cavity is scanned in a three-dimensional manner will be explained.

Figure 16:
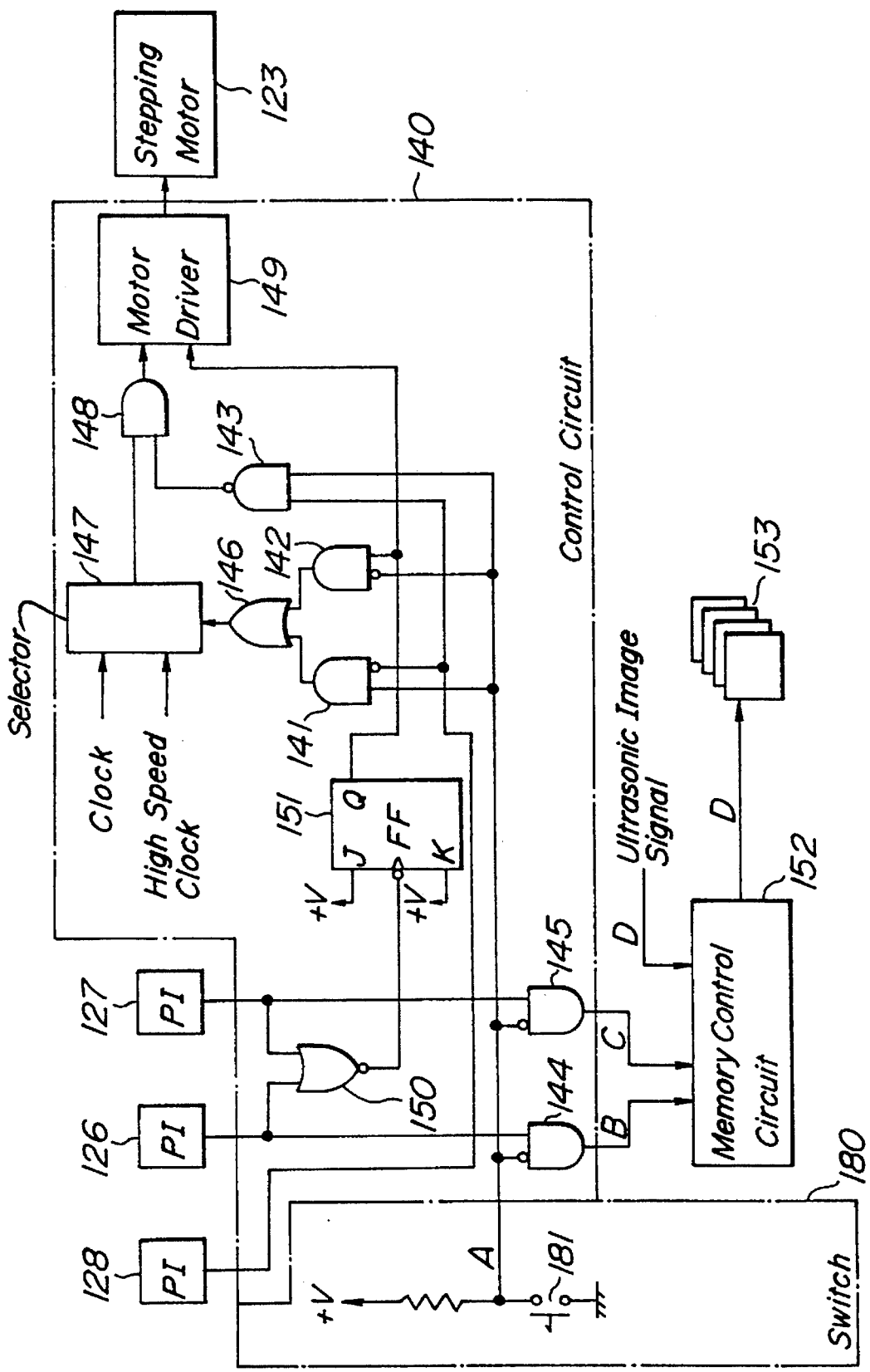
FIG. 16 is a circuit diagram depicting an embodiment of a part of the device shown in FIG. 15.

FIGS. 15 and 16 illustrate a first embodiment of the driving device according to the invention. In FIG. 15, within a sheath 113 of an ultrasonic probe 111, there is arranged a shaft 114, and an ultrasonic vibrating element 112 is secured to a distal end of the shaft 114. A proximal end of the shaft 114 is coupled with a connector 115 which is rotated together with the shaft and is arranged within a probe outer housing 118 to which the probe 111 is fixed. The probe outer housing 118 is detachably secured to a driving unit 116.

The driving unit 116 comprises an electric motor 119 which constitutes a first driving means. A connector 117 is coupled with the motor 119 by means of a driving force transmission shaft 120. The connector 117 is detachably coupled with the connector 115 on the side of the probe 111, so that the rotation of the motor 119 is transmitted to the ultrasonic vibrating element 112 by means of the shaft 120, connectors 117, 115 and shaft 114. At the same time, the connector 117 is moved linearly along the shaft 120, so that the ultrasonic vibrating element 112 is moved linearly. To this end, a flange 121 is formed on the connector 117 and a ball screw 122 is secured to the flange, the ball screw being coupled with an output shaft of a stepping motor 123 constituting a second driving means.

Within the driving unit 116, there are provided three photo interruptors 126, 127 and 128 for detecting a position of the flange 121 in the axial direction of the shaft 120. It should be noted that by detecting the position of the flange 121, it is possible to detect the position of the connector 117 in the axial direction of the shaft 120. These photo interruptors 126, 127 and 128 are arranged in this order viewed from the probe side and generate active signals H when they detect the flange 121 and generate non-active signals L when they do not detect the flange 121.

On the connectors 115 and 117 there are arranged electric contacts which are connected with each other when these connectors are coupled with each other. Signal wires or conductors for the element 112 are extended within the shaft 114 and are connected to the contacts on the connector 115. The contact provided on the connector 117 are connected to an observation unit 125 by means of cable (not shown) and slip ring 124 coupled with the shaft 120. In this manner, the ultrasonic vibrating element 112 can be electrically connected to the observation unit 125. The motor 119, stepping motor 123 and observation unit 125 are controlled by a driving control circuit 140, and the output signals of the photo interruptors 126, 127 and 128 are supplied to the control circuit 140. Further, to the control circuit 140 is connected an image pick-up start switch 180.

FIG. 16 is a circuit diagram illustrating a detailed construction of the control circuit 140 and image pick-up start switch 180. The image pick-up start switch 180 is formed by a contact non-return type in which a contact 181 is not automatically returned into an initial position even if a finger of the user is detached from the switch. The switch 180 is connected to non-inverted input of AND gate 141, inverted input of AND gate 142, one non-inverted input of NAND gate 143, inverted input of AND gate 144 and inverted input of AND gate 145. Outputs of the AND gates 141 and 142 are connected to inputs of OR gate 146, and an output of this OR gate is connected to a switching terminal of a selector 147.

The selector 147 functions to select either one of normal clock and high speed clock. When the signal applied at the switching terminal is H, the selector 147 selects the high speed clock and when the signal at the switching terminal is L, the normal clock is selected. The output clock selected by the selector 147 is supplied to one of the non-inverted inputs of AND gate 148. An output of this AND gate 148 is connected to a clock input terminal of a motor driver 149 for driving the stepping motor 123. In this manner, the stepping motor 123 is driven by the clock selected by the selector 147.

An output signal of the photo interruptor (PI) 128 is supplied to the inverted input of the AND gate 141 as well as to the other non-inverted input of the NAND gate 143. An output signal of the photo interruptor 126 is supplied to one of the non-inverted input of NOR gate 150 as well as to non-inverted input of the AND gate 144, and an output signal of the photo interruptor 127 is supplied to the other non-inverted input of the NOR gate 150 and to the non-inverted input of the AND gate 145. An output terminal of the NOR gate 150 is connected to a clock input of J-K flip-flop 151 whose J- and K-inputs are pulled up to a supply voltage +V and whose Q-output is connected to non-inverted input of the AND gate 142 as well as to a rotating direction control terminal of the motor driver 149.

An output terminal of the AND gate 144 is connected to a record start signal terminal of a memory control circuit 152 provided in the observation unit 125 shown in FIG. 15, and an output terminal of the AND gate 145 is connected to a record stop signal terminal of the memory control circuit 152. To the memory control circuit 152 is supplied an ultrasonic image signal which is obtained by processing the echo signal generated by the ultrasonic vibrating element 112. Under the control of the control signals supplied to the record start and stop signal terminals of the memory control circuit 152, the ultrasonic image signal is stored in an image memory 153.

In the present embodiment, a signal generated by an oscillator provided in the observation unit 125 is supplied to the ultrasonic vibrating element 112 to emit an ultrasonic wave toward the living body under inspection, and an ultrasonic wave reflected by the living body is received by the element 112 to produced the echo signal. The echo signal is processed by the observation unit 125 to display an ultrasonic image on a monitor not shown. The ultrasonic vibrating element 112 is rotated by the motor 119 by means of the shaft 120, connectors 117, 115 and shaft 114 to perform the radial scan. At the same time, the ultrasonic vibrating element 112 is moved linearly in a reciprocal manner by the stepping motor 123 by means of the ball screw 122, flange 121, connectors 117, 115 and shaft 114 to perform the linear scan. In this manner, the living body can be scanned by the ultrasonic wave in a three-dimensional manner. In the present embodiment, the three-dimensional scan is carried out in a helical manner.

When the contact 181 of the image pick-up start switch 180 is OFF, the image pick-up start signal A is H. In this case, as long as the photo interruptor 128 does not detect the flange 121 of the connector 117, the output signal of this photo interruptor is L, so that the output of the AND gate 141 is H and the signal of H is applied to the switching terminal of the selector 147 via the OR gate 146. Therefore, the selector 147 selects the high speed clock and the thus selected high speed clock is applied to one of the non-inverted inputs of the AND gate 148. Further, in this condition, the output signal of the NAND gate 143 is H, so that the AND gate 148 is driven into the open state and the high speed clock is applied to the clock input terminal of the motor driver 149 and the stepping motor 123 is driven at a high speed. In this manner, the ultrasonic vibrating element 112 is moved linearly at a high speed to effect the linear scan, while the element 112 is rotated at a given speed to perform the radial scan.

When the flange 121 is detected by the photo interruptor 128, the output signal of the NAND gate 143 is changed from H to L, so that the AND gate 148 is driven into a closed state and the rotation of the stepping motor 123 is stopped. Therefore, the ultrasonic vibrating element 112 performs only the radial scan at a position at which the flange 121 is detected by the photo interruptor 128.

In this condition, when the contact 181 of the image pick-up start switch 180 is closed by the operator, the image pick-up start signal A becomes L and the output signal of the NAND gate 143 becomes H. Therefore, the AND gate 138 is driven in to the open state and the high speed clock is supplied again to the clock input of the motor driver 149. Therefore, the stepping motor 123 is driven at the high speed and the ultrasonic vibrating element 112 is moved linearly to perform the three-dimensional scan.

When the flange 121 is detected by one of the photo interruptors 126 and 127, the output signal of the NOR gate 150 becomes L and the Q output signal of the J-K flip flop 151 is changed from H to L. Therefore, the control signal applied to the rotating direction control terminal of the motor driver 149 becomes L and the rotating direction of the stepping motor 123 is reversed, and thus the direction of the linear movement of the ultrasonic vibrating element 123 is reversed. After reversing the direction of the linear movement, the output signal of one of the photo interruptors 126 and 127 which detected the flange 121 is returned into L.

By repeating the above operation, it is possible to perform the three-dimensional scan, i.e. helical scan over a three-dimensional scan range shown in FIG. 15, while the ultrasonic vibrating element 112 is rotated as well as moved linearly in a reciprocal manner.

It is now assumed that when the Q output signal of the J-K flip flop 151 and thus the control signal applied to the rotating direction control terminal of the motor driver 149 is H, the flange 121 moves in a direction from the photo interruptor 127 to the photo interruptor 126, i.e. the ultrasonic vibrating element 112 is moved toward the distal end of the ultrasonic probe 111, then the output signal of the AND gate 142 is H when the contact 181 of the image pick-up start switch 180 is closed. Therefore, the output signal of the AND gate 142 is H and the high speed clock is selected by the selector 147 and the ultrasonic vibrating element 112 is moved linearly at a high speed. Contrary to this, when the Q output signal of the flip flop 151 is L, the ultrasonic vibrating element 112 is moved toward the proximal end of the ultrasonic probe 111. Then, the output signals of the AND gates 141 and 142 are L, so that the control signal to the switching terminal of the selector 147 becomes L and the normal clock is selected thereby. Therefore, the ultrasonic vibrating element 112 is moved linearly at a low speed.

In order to pick-up the echo data during the three-dimensional scanning, the contact 181 of the image pick-up start switch 180 is made ON, so that when the flange 121 is detected by the photo interruptor 126, the output signal of the AND gate 144 becomes H. Therefore, the record start signal H is supplied to the record start signal terminal of the memory control circuit 152 and the ultrasonic image signal D obtained by processing the echo signal produced by the ultrasonic vibrating element 112 is stored in the image memory 153. After that, when the flange 121 is detected by the photo interruptor 127, the output signal of the AND gate 145 becomes H and the record stop signal C is applied to the record stop signal terminal of the memory control circuit 152. Therefore, the storing of the ultrasonic image signal D into the image memory 153 is stopped. In this manner, for a time period during which the ultrasonic vibrating element 112 scans the three-dimensional region over the predetermined three-dimensional scan range shown in FIG. 15, the ultrasonic image signal of three-dimensional region is stored in the image memory 153.

In the present embodiment, the photo interruptor 128 determining the position of the radial scan is arranged at a middle point between the photo interruptors 126 and 127 determining the linear scan range, and thus prior to storing the echo data of three-dimensional region, only the radial scan is carried out at a middle of the linear scan range and the B-mode ultrasonic image is displayed on the monitor. Therefore, the operator can easily and accurately confirm a fact that a region of interest will be able to be contained in the echo data of three-dimensional region. After confirming this, the operator can operate the image pick-up start switch 180. In this manner, it is possible to display the three-dimensional image including the region of interest in a positive and reliable manner.

In the present embodiment, the ultrasonic vibrating element 112 is moved linearly at a low speed only during the storing of the echo data into the image memory 153 and for the remaining time period, the ultrasonic vibrating element is moved linearly at a high speed, and therefore the patient is sufficient to stop breath only during the storing of the echo signal.

In the above explained embodiment, the photo interruptor 128 determining the start point of the radial scan is arranged at a middle point between the photo interruptors 126 and 127 determining the linear scan range, but according to the invention the photo interruptor 128 may be provided at any position between the photo interruptors 126 and 127. Further, the position of the flange 121 may be detected by other detectors such as a limit switch.

Moreover, the image pick-up start switch 180 may be provided integrally with the ultrasonic probe 111, driving unit 116, observation unit 125 or control circuit 140. In the above embodiment, the echo data of three-dimensional region is stored during an interval in which the ultrasonic vibrating element 112 is linearly moved from the distal end to the proximal end of the ultrasonic probe 111, but according to the invention the echo data of the three-dimensional region may be stored during a time interval during which the ultrasonic vibrating element is moved from the proximal end to the distal end of the ultrasonic probe 111.

FIG. 17 is a cross sectional view showing a second embodiment of the driving device according to the invention. In the present embodiment, the photo interruptors 126, 127 and 128 in the previous embodiment are removed and there is provided an image pick-up start signal generating circuit 190 instead of the image pick-up start switch 180.

FIG. 18 is a block diagram showing an embodiment of the image pick-up start signal generating circuit 190 and driver control circuit 140. The image pick-up start signal generating circuit 190 comprises a return contact 191 which is normally driven into an ON terminal which is connected to a preset terminal of a flip-flop 192 whose OFF terminal is connected to a clear terminal of the flip-flop 192. A Q-output terminal of the flip-flop 192 is connected to a reset terminal of a timer circuit 193 as well as to one of non-inverted input terminals of AND gate 194. An output terminal of the timer circuit 193 is connected to a clock input terminal of J-K flip-flop 196 via an inverter 195. The image pick-up start signal generating circuit 190 further comprises a power ON preset circuit 197 whose output terminal is connected to the other non-inverted input terminal of the AND gate 194, and the output terminal of the AND gate 194 is connected to a preset terminal of a J-K flip-flop 196. The J-K flip-flop 196 has J and K input terminals having pulled up to power supply voltage +V. A Q-output terminal of the J-K flip-flop 196 is connected to an input terminal of a gate circuit 154 as well as to the non-inverted input terminal of the AND gate 158 provided in the driver control circuit 140.

In the driver control circuit 140, the clock signal is applied to the clock input terminal of the gate circuit 154, and an output terminal of the gate circuit 154 is connected to clock input terminals of the motor driver 149 for driving the stepping motor 123, gate circuit 155 and counter 156. An output terminal of the counter 156 is connected to gate on-off control terminals of the gate circuits 154 and 155. An output terminal of the gate circuit 155 is connected to a clock input terminal of a J-K flip-flop 157. The J-K flip-flop 157 has J and K input terminals having been pulled up to the power supply voltage +V. An output terminal of the J-K flip-flop 157 is connected to a rotational direction control terminal of the motor driver 149, summation and subtraction control terminal of the counter 156 and a non-inverted input terminal of AND gate 158.

An output terminal of the AND gate 158 is connected to a record signal terminal of a memory control circuit 152 provided in the observation unit 125. To this memory control circuit 142 is supplied with the ultrasonic image signal D which is obtained by processing the echo signal produced by the ultrasonic vibrating element 112 shown in FIG. 16. The ultrasonic image signal D is stored in an image memory 153.

Also in the present embodiment, a signal generated by an oscillator (not shown) provided in the observation unit 125 is supplied to the ultrasonic vibrating element 112 to emit the ultrasonic wave toward the living body and the ultrasonic wave reflected by the living body is received by the element to produce the echo signal. The echo signal is then processed by the observation unit 125 to display the ultrasonic image of the living body on a monitor not shown. The ultrasonic vibrating element 112 is rotated by the motor 119 via the shaft 120, connectors 117 and 115 and shaft 114 to effect the radial scan. At the same time, the ultrasonic vibrating element 112 is moved linearly by the stepping motor 123 via the ball screw 122, flange 121, connectors 17 and 115 and shaft 114 to perform the linear scan. In this manner, the living body can be scanned by the ultrasonic wave three-dimensionally.

At first, the operation of the image pick-up start signal generating circuit 190 will be explained.

When a power switch is turned ON, the output of the power ON preset circuit 197 is gradually increased toward the logic high level H. When the output of this circuit 197 has arrived at the level H, the J-K flip-flop 196 is preset by means of the AND gate 194, and its Q output A (image pick-up start signal) becomes H. During this condition, after the return contact 191 has been made OFF, when it is returned into the ON state, the rising edge signal is applied to the reset terminal of the timer circuit 193, so that the output of the timer circuit is in L level for a given time period. The output of the timer circuit 193 is supplied to the clock input terminal of the J-K flip-flop 196 as a trailing edge signal by means of the inverter 195. Therefore, the image pick-up start signal A is changed from H into L.

Next the operation of the driver control circuit 140 will be explained.

In the driver control circuit 140, as long as the image pick-up start signal A supplied from the image pick-up start signal generating circuit 190 is in the H level, the gate circuit 154 remains open until a count value supplied from the counter 156 to the gate ON-OFF control terminal becomes identical with a preset value $\gamma$, so that the gate circuit 154 produces the clock signal supplied to the clock input terminal. This clock signal is supplied to the clock input terminal of the motor driver 149 and the stepping motor 123 is driven in one direction and the ultrasonic vibrating element 112 is moved linearly along the axis of the ultrasonic probe 111. The output produced by the gate circuit 154 is supplied to the clock input terminal of the gate circuit 155 as well as to the clock input terminal of the counter 156. Therefore, the clock signals are counted by the counter 156. When the count value of the counter 156 becomes identical with the predetermined value $\gamma$, the gate circuit 154 is driven into the closed state and the clock signals are no longer supplied to the clock input terminal of the motor driver 149, so that the stepping motor 123 is stopped. Therefore, the linear scan is stopped and only the radial scan is carried out at a position at which the count value is equal to the preset value $\gamma$.

Once the return contact 191 of the image pick-up start signal generating circuit 190 is in the OFF state and the image pick-up start signal A becomes L level, the gate circuit 154 becomes in the open state irrespective of the count value of the count 156. Therefore, the clock signal is supplied to the clock input terminal of the motor driver 149 and the stepping motor 123 is driven. Therefore, the ultrasonic vibrating element 112 is moved linearly along the axis of the ultrasonic probe 111 to perform the linear scan.

The gate circuit 155 has preset values $\alpha$ and $\beta$ ($\alpha<\gamma<\beta$) and becomes into the open state only when the count value of the counter 156 becomes identical with $\alpha$ and $\beta$, so that one clock pulse is applied to the clock input terminal of the J-K flip-flop 157. Then, the Q output of the J-K flip-flop 157 is inverted, and thus the rotating direction of the stepping motor 123 is reversed and the ultrasonic vibrating element 112 is moved linearly in an opposite detection. The Q output of the J-K flip-flop 157 is also applied to the up-down control terminal of the counter 156, so that when the Q output is reversed, the counter 156 is also changed from the count-up to the count-down or vise versa. Therefore, the count value of the counter 156 is reciprocally changed between $\alpha$ and $\beta$, so that the ultrasonic vibrating element 112 is linearly moved in a reciprocal manner over the linear scan range as illustrated in FIG. 17.

Upon storing the echo data during the three-dimensional scan, the Q output of the J-K flip-flop 157 and the image pick-up start signal A are applied to the AND gate 158, so that the output E of the AND gate 158 becomes H only for a time period during which the ultrasonic vibrating element 112 is moved in a first direction during the three-dimensional scan. Therefore, the ultrasonic image signal D obtained by processing the echo signal is stored in the image memory 153 under the control of the memory control circuit 152 during a time interval during which the record signal E is in the high level H. In this manner, the image memory 153 stores the ultrasonic image signal D which corresponds to a forward or backward movement of the three-dimensional scan while the ultrasonic vibrating element 112 is moved linearly toward the distal end or proximal end of the probe 111.

In the present embodiment, it is no longer necessary to use the photo interruptors 126, 127 and 128 provided in the previous embodiment illustrated in FIGS. 15 and 16, but the position of the radial scan and the range of the linear scan can be determined. Furthermore, when the value $\gamma$ is set to a middle point between the values $\alpha$ and $\beta$ provided in the gate circuit 155 for determining the linear scan range, it is possible to display the B mode radial scan image at the middle point in the linear scan range. Thus, the it is positively and easily confirmed whether or not a region of interest is contained in the three-dimensional scan, and after confirmation the return contact 191 may be operated. In this manner, the three-dimensional image of the region of interest can be displayed.

It should be noted that the value $\gamma$ is not always necessary to be set at the middle point in the linear scan range determined by the values $\alpha$ and $\beta$ in the gate circuit 154, but according to the invention, the value $\gamma$ may be set at any point within the linear scan range except for both boundaries thermal. Further, the image pick-up start signal generating circuit 190 may be provided integrally with the ultrasonic probe 111, driving unit 116, observation unit 154 or driver control circuit 140. Moreover, plural sets of the values $\gamma$, $\alpha$ and $\beta$ may be previously prepared and any desired values may be selected in accordance with a position or organ of the living body to be inspected and/or a kind of the ultrasonic vibrating element to be used.

In the above mentioned embodiments of the driving device according to the invention, the three-dimensional scan is performed by a combination of the radial scan and the linear scan. According to the invention, it is also possible to perform the three-dimensional scan by a combination of a sector scan and the linear scan as illustrated in FIG. 19. That is to say, the ultrasonic vibrating element 112 is swung by a given angle by means of a motor 119 to perform the sector scan, while the ultrasonic vibrating element is linearly moved by the stepping motor 123.

It should be further noted that the three-dimensional scan may be carried out by a combination of first and second scans which are perpendicular to each other or a combination of first and second linear scan which are perpendicular to each other.

As explained above, according to the invention, the operator can see the B-mode ultrasonic tomographic image by the first scan at a position within the scan range of the second scan until the image pick-up start signal is generated, so that the operator can confirm whether or not the region of interest is contained in the three-dimensional scan. Therefore, the three-dimensional ultrasonic image of the region of interest can be easily and promptly obtained.

What is claimed is:

1. An ultrasonic image diagnosing apparatus comprising:

an ultrasonic probe means for emitting an ultrasonic wave to scan a living body in a three-dimensional manner and receiving an ultrasonic wave reflected by the living body to derive echo data of a three-dimensional region;

a three-dimensional data storing means for storing said echo data of said three-dimensional region derived from the ultrasonic probe means;

a cross sectional position setting means for setting a desired cross sectional position within the echo data to determine a display range of the echo data of said three-dimensional region;

a cross sectional position storing means for storing data representing said cross sectional position set by said cross sectional position setting means;

a surface position extracting means for extracting surface position data representing a surface of an object under inspection from the echo data of said three-dimensional region;

a surface position data storing means for storing said surface position data of said surface;

a three-dimensional image data producing means for producing three-dimensional image data by converting the echo data within the three-dimensional display range at the cross sectional position set by said cross sectional position setting means into two-dimensional perspective image data seen from a given direction;

a shade adding means for adding shade to said surface of the object, indicated by said surface position data, to derive surface image data;

a surface composing means for producing composed three-dimensional image data by composing said three-dimensional image data formed by said three-dimensional image data producing means and the surface image data having said shade added thereto, at a position corresponding to said surface represented by said surface position data; and a display means for receiving said composed three-dimensional image data to display a three-dimensional image.

2. An apparatus according to claim 1, wherein said ultrasonic probe means comprises an ultrasonic vibrating element which emits said ultrasonic wave and is adapted to be arranged at a distal end of an insertion section of an endoscope to be inserted into a cavity of a living body, and a scanning means for driving said ultrasonic vibrating element such that a first cross section as well as a second cross section perpendicular to said first cross section are scanned by the ultrasonic wave to perform a three-dimensional scan.

3. An apparatus according to 2, wherein said scanning means comprises a first driving means for driving the ultrasonic vibrating element such that the first cross section is scanned by the ultrasonic wave, and a second driving means for driving the ultrasonic element such that the second cross section is scanned by the ultrasonic wave.

4. An apparatus according to claim 3, wherein said first driving means is constructed such that the ultrasonic vibrating element is rotated within the ultrasonic probe means about an axis parallel with a longitudinal axis of the ultrasonic vibrating probe means to perform a radial scan, and said second driving means is constructed such that the ultrasonic vibrating element is moved linearly in a direction parallel with said axis to perform a linear scan.

5. An apparatus according to claim 3, wherein said first driving means is constructed such that the ultrasonic vibrating element is swung within the ultrasonic probe means about an axis parallel with a longitudinal axis of the ultrasonic vibrating probe means to perform a sector scan, and said second driving means is constructed such that the ultrasonic vibrating element is moved linearly in a direction parallel with said axis to perform a linear scan.

6. An apparatus according to any one of claims 1 to 5, wherein said three-dimensional image data producing means comprises a shading means for applying a shading to a cross section in the displayed three-dimensional image.

7. An apparatus according to claim 6, wherein said cross sectional position setting means is constructed such that a cross sectional position is set for cross sectional images except for the lowermost cross sectional image so that the three-dimensional display image displayed on the displaying means contains the lowermost cross sectional image.

8. An apparatus according to claim 7, further comprising a first image data producing means for processing the echo data obtained for a time period during which said first cross section is scanned by the ultrasonic vibrating element prior to picking-up the echo data of three-dimensional region and producing first image data representing a first ultrasonic tomographic image to be displayed by said display means, a second cross sectional position setting means for setting a desired cross sectional position in said displayed first ultrasonic tomographic image, and a second image data producing means for processing the echo data of three-dimensional region during the three-dimensional scan by scanning said first and second cross sections and producing second image data representing a second ultrasonic tomographic image at the cross sectional position set by said second cross sectional position setting means.

9. An apparatus according to claim 8, said second cross sectional position setting means comprises a means for displaying a mark representing a position of a cross section in superimposition upon the first ultrasonic tomographic image displayed on the displaying means, and a means for changing a relative angular position between said mark and said first ultrasonic tomographic image.

10. An apparatus according to claim 8, said second cross sectional position setting means is constructed to produce image data representing the second ultrasonic tomographic image at said cross sectional position set by said second cross sectional position setting means and at least one ultrasonic tomographic image which is shifted by a predetermined angle with respect to said second ultrasonic tomographic image, said ultrasonic tomographic images being simultaneously displayed on the displaying means.

11. An apparatus according to any one of claims 1 to 5, wherein said cross sectional position setting means is constructed such that a cross sectional position is set for cross sectional images except for a lowermost cross sectional image within the echo data so that the three-dimensional display image displayed on the displaying means contains the lowermost cross sectional image.

12. An apparatus according to claim 7, further comprising a first image data producing means for processing the echo data obtained for a time period during which said first cross section is scanned by the ultrasonic vibrating element prior to picking-up the echo data of three-dimensional region and producing first image data representing a first ultrasonic tomographic image to be displayed by said display means, a second cross sectional position setting means for setting a desired cross sectional position in said displayed first ultrasonic tomographic image, and a second image data producing means for processing the echo data of three-dimensional region during the three-dimensional scan by scanning said first and second cross sections and producing second image data representing a second ultrasonic tomographic image at the cross sectional position set by said second cross sectional position setting means.

13. An apparatus according to claim 12, said second cross sectional position setting means comprises a means for displaying a mark representing a position of a cross section in superimposition upon the first ultrasonic tomographic image displayed on the displaying means, and a means for changing a relative angular position between said mark and said first ultrasonic tomographic image.

14. An apparatus according to claim 12, said second cross sectional position setting means is constructed to produce image data representing the second ultrasonic tomographic image at said cross sectional position set by said second cross sectional position setting means and at least one ultrasonic tomographic image which is shifted by a predetermined angle with respect to said second ultrasonic tomographic image, said ultrasonic tomographic images being simultaneously displayed on the displaying means.

15. An apparatus according to any one of claims 2 to 5, further comprising a first image data producing means for processing the echo data obtained for a time period during which said first cross section is scanned by the ultrasonic vibrating element prior to picking-up the echo data of said three-dimensional region and producing first image data representing a first ultrasonic tomographic image to be displayed by said display means, a second cross sectional position setting means for setting a desired cross sectional position in said displayed first ultrasonic tomographic image, and a second image data producing means for processing the echo data of said three-dimensional region during the three-dimensional scan by scanning said first and second cross sections and producing second image data representing a second ultrasonic tomographic image at the cross sectional position set by said second cross sectional position setting means.

16. An apparatus according to claim 15, wherein said second cross sectional position setting means comprises a means for displaying a mark representing a position of a cross section in superimposition upon the first ultrasonic tomographic image displayed on the displaying means, and a means for changing a relative angular position between said mark and said first ultrasonic tomographic image.

17. An apparatus according to claim 15, wherein said second cross sectional position setting means is constructed to produce image data representing the second ultrasonic tomographic image at said cross sectional position set by said second cross sectional position setting means and at least one ultrasonic tomographic image which is shifted by a predetermined angle with respect to said second ultrasonic tomographic image, said ultrasonic tomographic images being simultaneously displayed on the displaying means.

18. An apparatus according to any one of claims 1 to 5, wherein said surface position extracting means comprises a means for performing a threshold treatment for the echo data of said three-dimensional region by using a threshold value, a means for setting said threshold value to be used in said threshold treatment, a means for denoting a given area in a cross section of a wall forming a cavity of the living body on a given tomographic image at a given cross sectional position comprising said three-dimensional image data, and a means for comparing the cross sectional image on which the wall of said cavity is denoted and a cross sectional image adjacent to said cross sectional image and judging portions in these cross sectional images which are common to these images as a wall of the cavity.

19. An apparatus according to claim 6, further comprising a first image data producing means for processing the echo data obtained for a time period during which said first cross section is scanned by the ultrasonic vibrating element prior to picking-up the echo data of three-dimensional region and producing first image data representing a first ultrasonic tomographic image to be displayed by said display means, a second cross sectional position setting means for setting a desired cross sectional position in said displayed first ultrasonic tomographic image, and a second image data producing means for processing the echo data of three-dimensional region during the three-dimensional scan by scanning said first and second cross sections and producing second image data representing a second ultrasonic tomographic image at the cross sectional position set by said second cross sectional position setting means.

20. An apparatus according to claim 19, said second cross sectional position setting means comprises a means for displaying a mark representing a position of a cross section in superimposition upon the first ultrasonic tomographic image displayed on the displaying means, and a means for changing a relative angular position between said mark and said first ultrasonic tomographic image.

21. An apparatus according to claim 19, said second cross sectional position setting means is constructed to produce image data representing the second ultrasonic tomographic image at said cross sectional position set by said second cross sectional position setting means and at least one ultrasonic tomographic image which is shifted by a predetermined angle with respect to said second ultrasonic tomographic image, said ultrasonic tomographic images being simultaneously displayed on the displaying means.

22. An apparatus according to any one of claims 3 to 5, further comprising
    an image pick-up start signal generating means for generating an image pick-up start signal for initiating pick-up of echo data of said three-dimensional region; and
    a control means for controlling said first and second driving means such that prior to generation of said image pick-up start signal, only said first scan is performed by said first driving means on said first cross section at a position which is within a scanning range on said second cross section but which is not at either end of said second cross section, and after generation of said image pick-up start signal, the echo data of said three-dimensional region is stored.

23. An apparatus according to claim 22, wherein said control means is constructed such that prior to said generation of the image pick-up start signal, said first scan is carried at an approximately middle point within the scanning range on the second cross section.

24. An ultrasonic image diagnosing apparatus for effecting emission and reception of an ultrasonic wave with respect to a living body, picking-up echo data of a three dimensional region, and displaying an ultrasonic image within the living body by processing the picked-up echo data, said apparatus comprising:

a three-dimensional data storing means for storing said echo data of said three-dimensional region;

a cross sectional position setting means for setting a desired cross sectional position within said echo data of said three-dimensional region;

a surface position extracting means for extracting a desired position of a surface of an object within the echo data of said three-dimensional region;

a surface position storing means for storing the extracted surface position data;

an inside data storing means for storing inside data comprising three-dimensional data representing an area within the living body except for said surface having said desired position extracted by said extracting means;

a shading means for effecting a shading treatment upon a surface which is denoted by surface position data stored in said surface position storing means;

an image composing means for composing surface image data with the shading treatment effected by said shading means and the three-dimensional image data to produce composed image data;

a data cutting means for cutting the surface position data and said inside data or said composed image data at said cross sectional position set by said cross sectional position setting means; and a display means for converting said composed image data into two dimensional projection data to display a three-dimensional image representing said composed image data.

25. An ultrasonic image diagnosing apparatus for performing a three-dimensional scan, said apparatus comprising:

an ultrasonic vibrating element;

first and second driving means for respectively driving said vibrating element to perform first and second scans on first and second cross sections of a body under inspection, said first and second cross sections being approximately perpendicular to one another, to obtain a three-dimensional ultrasonic image;

an image pick-up start signal generating means for generating an image pick-up start signal for initiating pick-up of echo data of a three-dimensional region of said body; and a control means for controlling said first and second driving means such that prior to generation of said image pick-up start signal, only said first scan is performed by said first driving means on said first cross section at a position which is within a scanning range on said second cross section but which is not at either end of said second cross section, and after generation of said image pick-up start signal, the echo data of said three-dimensional region is stored.

26. An apparatus according to claim 25, wherein said first cross-section is along a radial dimension of said body and said second cross-section is along a longitudinal axis of said body.

27. An apparatus according to claim 25, wherein said first cross-section is along a lateral dimension of said body and said second cross-section is along a longitudinal axis of said body.

28. An apparatus according to claim 25, wherein said first scan is a radial scan and said second scan is a linear scan performed along an axis about which said radial scan is performed.

* * * * *